US006413523B1

(12) United States Patent
Clements

(10) Patent No.: US 6,413,523 B1
(45) Date of Patent: Jul. 2, 2002

(54) **PHARMACEUTICAL COMPOSITION OF *ESCHERICHIA COLI* HEAT-LABILE ENTEROTOXIN ADJUVANT AND METHODS OF USE**

(75) Inventor: John D Clements, New Orleans, LA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 08/394,522

(22) Filed: Feb. 23, 1995

Related U.S. Application Data

(63) Continuation of application No. 08/000,906, filed on Jan. 6, 1993, now abandoned, which is a continuation-in-part of application No. 07/360,662, filed on Jun. 2, 1989, now abandoned.

(51) Int. Cl.[7] ...................... A61K 39/108; A61K 39/02; A61K 39/385
(52) U.S. Cl. ................ 424/241.1; 424/93.1; 424/93.48; 424/197.11; 424/234.1; 424/236.1
(58) Field of Search ...................................... 424/236.1

(56) References Cited

U.S. PATENT DOCUMENTS

| | | | |
|---|---|---|---|
| 4,053,584 A | 10/1977 | Dobrescu et al. | 424/92 |
| 4,314,993 A | 2/1982 | Wijnendaele | 424/92 |
| 4,411,888 A * | 10/1983 | Klipstein et al. | 424/92 |
| 4,488,991 A | 12/1984 | Tolman et al. | 260/112 |
| 4,545,931 A | 10/1985 | Houghten | 260/112.5 |
| 4,758,655 A | 7/1988 | Houghten | 530/324 |
| 4,808,700 A | 2/1989 | Anderson et al. | 530/403 |
| 4,886,663 A | 12/1989 | Houghten | 424/88 |
| 4,971,794 A | 11/1990 | Linggood et al. | 424/92 |
| 5,026,557 A | 6/1991 | Estis et al. | 424/450 |
| 5,182,109 A * | 1/1993 | Tamura et al. | 424/92 |

FOREIGN PATENT DOCUMENTS

WO        8606635    * 12/1986 ......... A61K/34/385

OTHER PUBLICATIONS

Challacombe and Tomasi, 1980, J. Exp. Med. 152: 1459–1472.
Siskind, 1984, In: Fundamental Immunology (Ed. Paul) Raven Press, New York pp. 537–558.
Green and Ptak, 1986, Immunol. Today 7: 81–87.
LaFont, et al., 1982, J. Exp. Med. 142: 1573–1578.
Suzuki, 1986, Nature 320: 451–454.
Elson and Ealding, 1984a, J. Immunol. 132: 2736–2741.
Finkelstein, 1973, CRC Crit. Rev. Microbiol. 2: 553–623.
In: Mechanisms in Bacterial Toxicology (Ed. Bemheiner) John Wiley and Sons, Inc., New York, pp. 53–84).
Clements and Finkelstein, 1979 Infect. Immun. 24: 760–769.
Clements et al., 1980, Infect. Immun. 29: 91–97.
Clements et al., 1983, Infect. Immun. 40: 653–658.
Clements and El–Morshidy, 1983, Infect. Immun. 46: 564–569.
Frantz et al., 1987, Infect. Immun. 55: 1077–1084.
Hussaini and Sawtell, 1986, Dev. Biol. Stand. 64: 261–269.
Spiegel et al., 1985, Science 230: 1285–1287.
Elson and Ealding, 1984b, J. Immunol. 133: 2892–2897.
McKenzie and Halsey, 1984, J. Immunol. 133: 1808–1824.
Vaughan et al., 1980, Nature 226: 658–659.
Greenough, 1970, J. Infect. Dis. 121: 5111–5114.
Shaefer et al., 1970, Proc. Natl. Acad. Sci. U.S.A. 67: 851–856.
Donta et al., 1973, Nature (New Biol.) 243: 246–247.
Donta et al., 1974, Science 183: 334–336.
Guerrant et al., 1974, Infect. Immun. 10: 320–327.
Nozawa et al., 1975, Infect. Immun. 12: 621–624.
Hynie et al., 1974, Toxicon 12: 173–179.
Kantor et al., 1975, J. Infect Dis. 133: 522–532.
Kantor et al., 1974, Infect. Immun. 9: 1003–1010.
Zenser and Metzger, 1974, Infect. Immun. 10: S03–S09.
Rappaport and Grant, 1974, Nature 248: 73–75.
Lycke et al., 1989, J. Immunol. 142: 20–27.
Clements et al Abstracts of the Annual Meeting of the ASM p. 44 Abstr. B–91.*
Clements et al Vaccine 6:269–277, 1988.*
Clements et al, Immunopharmacology of Infectious Diseases: Vaccine Adjuvants and Modulators of Nonspecific Resistance pp. 139–154, 1987.*
Childness et al Abstracts of the Annual Meeting of the ASM p. 316 Abstr. S–6.*
Lycke et al Immunology 1986 vol. 59 pp. 301–308 Strong Adjuvant Properties of Cholera Toxin on Gut Musocal Immune Responses to Orally Presented Antigens.*
Clements (I) I & I 1979 pp. 760–769 vol. 24.*
Clements (2) I & I 1980 pp. 91–97 vol. 29.*

* cited by examiner

*Primary Examiner*—Rodney P Swartz
(74) *Attorney, Agent, or Firm*—A. D. Spevack; Thomas E. McDonnell

(57) ABSTRACT

Novel immunoregulatory utilities of *Escherichi coli* heat-labile enterotoxin (LT) are disclosed. This enterotoxin can be used in combination with an unrelated antigen to achieve a higher immune response to said antigen when administered as part of an oral vaccine preparation. By way of example, the efficacy of oral adjuvant therapy of LT in the development of immunological protection against herpes simplex virus was examined. In addition, the ability of LT to influence the induction and maintenance of tolerance in animals primed orally with two unrelated protein antigens administered simultaneously, OVA and BSA was examined. Simultaneous administration of LT with OVA was shown to prevent the induction of tolerance to OVA and to increase the serum anti-OVA IgG response to 30–90 fold over PBS primed and OVA primed animals, respectively.

18 Claims, 15 Drawing Sheets

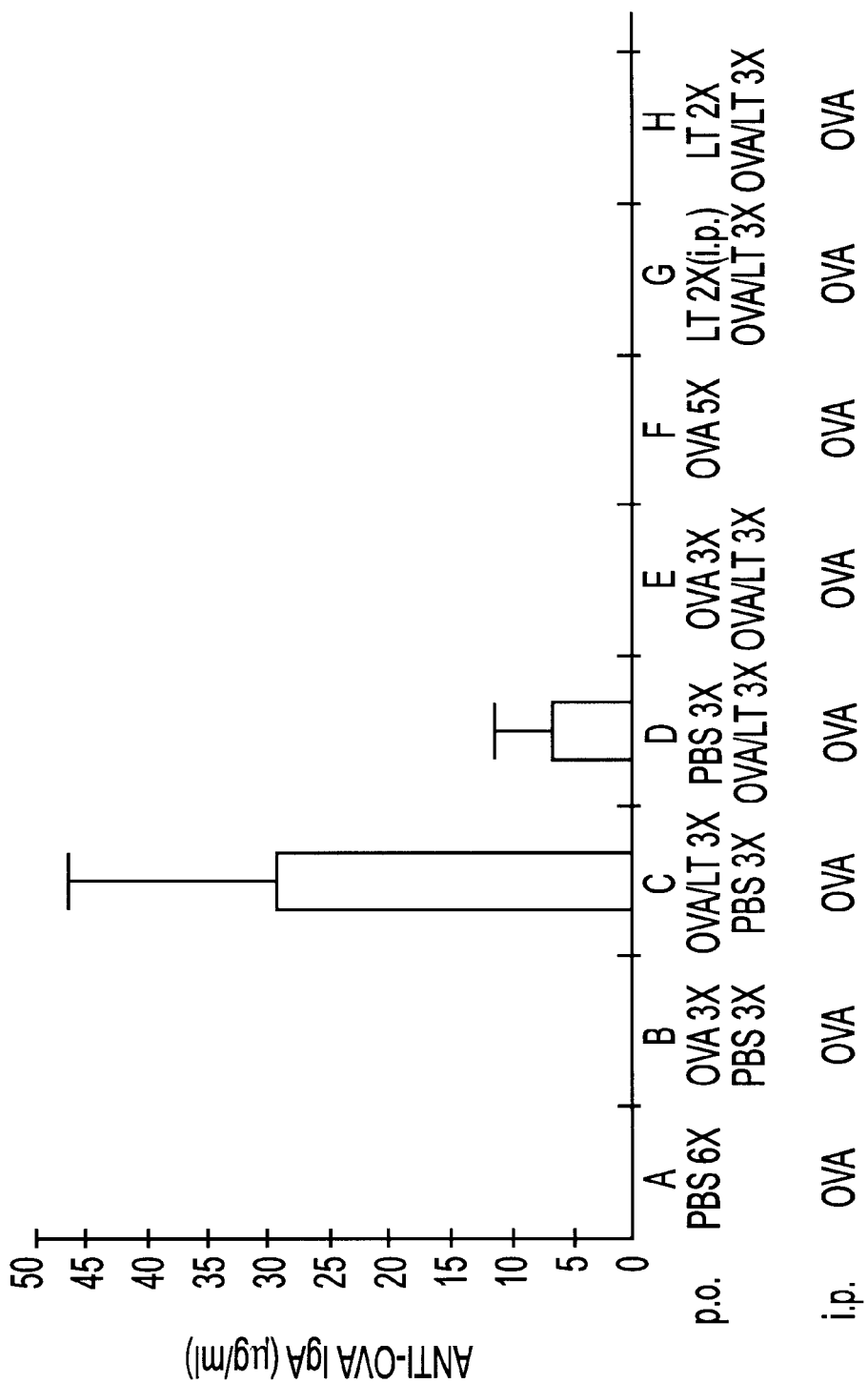

Figure 1:
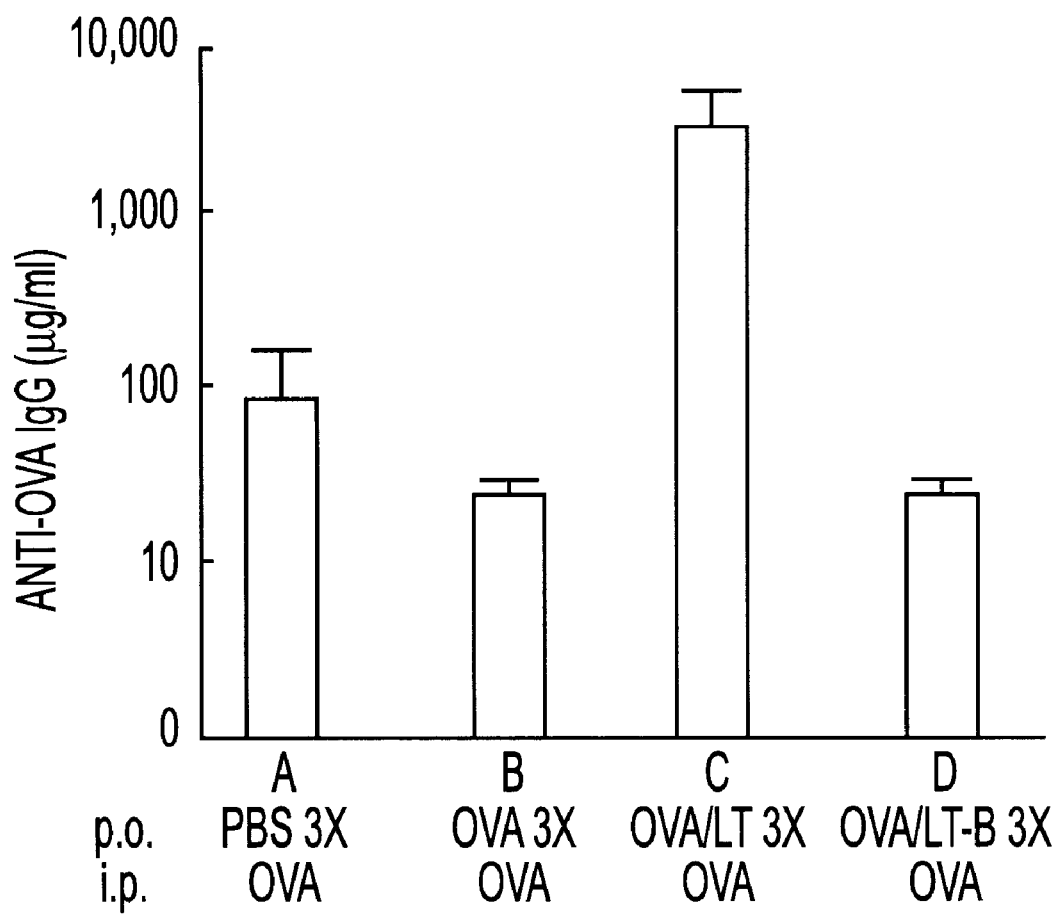

PHARMACEUTICAL COMPOSITION OF ESCHERICHIA COLI HEAT-LABILE ENTEROTOXIN ADJUVANT AND METHODS OF USE

RELATED APPLICATIONS

This application is a continuation of U.S. patent application Ser. No. 08/000,906 filed Jan. 6, 1993, now abandoned, which, in turn, is a continuation-in-part of U.S. patent application Ser. No. 07/360,662 filed Jun. 2, 1989, now abandoned.

1. INTRODUCTION

The present invention is directed towards the adjuvant activity of *Escherichia coli* heat-labile enterotoxin (LT) administered via the oral route. The invention is demonstrated by way of examples in which the efficacy of LT as an adjuvant for peptide, polysaccharide and for non-living microbial antigens is examined by in vivo and in vitro assay systems. With respect to peptide antigens, the capacity of LT to enhance serum IgG and mucosal IgA antibodies is demonstrated. With respect to microbial antigens, the capacity of LT to facilitate induction of long-lasting, specific resistance to microbial challenge is demonstrated.

Pursuant to the provisions of 35 U.S.C. §202(c), it is hereby acknowledged that the Government has certain rights in this invention, which was made in part with funds from the Department of the Navy.

2. BACKGROUND OF THE INVENTION
2.1. ADJUVANT ACTIVITY AND INFLUENCES ON TOLERANCE BY LT

Oral immunization can lead to loss of systemic reactivity in response to subsequent parenteral injection of the specific antigen (Challacombe and Tomasi, 1980, J. Exp. Med. 152:1459–1472). This phenomenon of immune tolerance after ingestion of antigen has been shown to occur in numerous animal models. A variety of effects may account for this phenomenon, including (a) antigen overload, (b) induction of antigen-specific suppressor T cells, and (c) clonal deletion of antigen-specific T and B cells [recently reviewed by Siskind] (Siskind, 1984, In: Fundamental Immunology (Ed. Paul) Raven Press, New York, pp. 537–558). The abrogation of tolerance (or prevention of its induction) has also been widely examined (Green and Ptak, 1986, Immunol. Today 7:81–87; La Tont, et al., 1982, J. Exp. Med. 142:1573–1578; Suzuki, 1986, Nature 320:451–454). In general, it has been observed that the the ability to influence induction of tolerance depends upon the cellular basis of the state of tolerance. Tolerance can be either complete or partial, and is influenced by antigen dose and characteristics, route of administration, physiological state of the organism, and genetic characteristics of the organism. It has also been shown that tolerance can be terminated or prevented by various manipulations, depending upon the cellular basis of the state of tolerance.

Recently it has been demonstrated that administration of cholera toxin (CT) can abrogate oral tolerance to an unrelated antigen (Elson and Ealding, 1984a, J. Immunol. 132:2736–2741). CT, an 84,000 dalton polymeric protein produced by *Vibrio cholerae*, consists of two subunits, designated A and B. The 56,000 dalton B subunit binds the toxin to its cell surface receptor, the monosialosylganglioside $G_{M1}$, and facilitates the penetration of the toxic 28,000 dalton A subunit into the cell. The A subunit catalyzes the ADP-ribosylation of the stimulatory GTP-binding protein ($G_S$) in the adenylate cyclase enzyme complex and this results in increasing intracellular levels of adenosine 3′, 5′-cyclic monophosphate (cAMP) (Finkelstein, 1973, CRC Crit. Rev. Microbiol. 2:553–623; In Mechanisms of Bacterial Toxinology (Ed. Bemheimer) John Wiley and Sons, Inc., New York, pp. 53–84). Some strains of *Escherichia coli* produce an immunologically and structurally related heat-labile enterotoxin (LT) that has the same subunit organization and arrangement as CT and that works by the same mechanism of action (Clements and Finkelstein, 1979, Infect. Immun. 24:760–769; Clements et al. 1980, Infect. Immun. 29:91–97). Although there are many similarities between CT and LT, there are also immunologic and structural differences between the two toxins (Clements and Finkelstein, 1979; Clements et al., 1980). It should be noted that the relative immunoregulatory potential of LT has not been thoroughly investigated. Recently, a clone of *E. coli* that produces only the binding subunit of the LT toxin (LT-B) was developed (Clements et al., 1983, Infect. Immun. 40: 653–658; Clements and El-Morshidy, Infect. Immun. 46: 564–569).

*Escherichia coli* heat-labile enterotoxin and heat-stable enterotoxin have previously been used in compositions that are effective in providing immunologic protection in mammals against acute diarrheal disease caused by enterotoxigenic strains of *E. coli*. See U.S. Patents 4,053,584; 4,314,993; and 4,411,888 which are incorporated herein by reference; and Frantz et al., 1987, Infect. Immun. 55: 1077–1084, Hussaini and Sawtell, 1986, Dev. Biol. Stand. 64: 261–269.

Although the mechanism for abrogation of tolerance by CT is unknown, it is presumed to result from an alteration of the regulatory environment in the gut associated lymphoid tissue, shifting it toward responsiveness (Elson and Ealding, 1984a). It was previously reported that both subunits of CT (and also of LT) have immunoregulatory potential. The binding subunit can mediate thymocyte proliferation (Spiegel et al., 1985, Science, 230:1285–1287) and act as an efficient carrier for stimulation of anti-hapten IgA responses to unrelated antigens (Elson and Ealding, 1984b, J. Immunol. 133: 2892–2897; McKenzie and Halsey, 1984, J. Immunol. 133: 1808–1824). The A subunit, as mentioned above, stimulates adenylate cyclase activity. CT and LT have been shown to stimulate lipolytic activity of isolated epididymal fat cells from rats (Vaughan et al., 1980, Nature 226:658–659; Greenough, 1970, J. Infect. Dis. 121:5111–5114), elevate cAMP levels in intestinal tissues in vivo (Shafer et al., 1970 Proc. Nat'l. Acad. Sci. USA. 67:851–856), increase delta-4, 3-ketosteroids and induce morphologic alterations in cultured mouse Y-1 adrenal tumor cells (Donta et al., 1973, Nature (New Biol.) 243:246–247; Donta et al., 1974, Science 183:334–336), and to increase accumulation of CAMP and induce morphologic alterations in cultured Chinese hamster ovary cells (Guerrant et al., 1974, Infect. Immun. 10:320–327). Cultured fibroblasts respond with increased cAMP and increased collagen synthesis (Guerrant et al., 1974) cell elongation and adhesion to substrate (Nozawa et al. 1975, Infect. Immun. 12:621–624) as well as by inhibition of nucleotide and amino acid transport and protein synthesis. These toxins have also been shown to stimulate basal adenylate cyclase activity in liver with a concomitant decrease in hepatic glycogen (Hynie et al., 1974, Toxicon 12:173–179), to stimulate adenylate cyclase activity of human embryonic intestinal epithelial cells in culture (Kantor, 1975, J. Infect. Dis. 133:522–532; Kantor et al., 1974, Infect, Immun. 9:1003–1010), and to increase membrane adenylate cyclase activity in mouse thymocytes (Zenser and Metzger 1974, Infect. Immun. 10:503–509) and rat pituitary cells (Rappaport and Grant, 1974, Nature 248:73–75). Presumably, because of the ubiquity of the $G_{M1}$ ganglioside in cell membranes, CT and LT have been found to have a broad spectrum of activity and, in fact, elevate intracellular levels of cAMP in virtually every mammalian tissue tested (Kantor, 1975). It should be noted that CT has been reported to have limited adjuvant activity (Lycke et al., 1989, J. Immunol. 142:20–27) and is able to abrogate tolerance to unrelated antigens (Elson and Ealding, 1984b).

In an abstract for the 88th Annual Meeting of the American Society for Microbiology, May 8–13, 1988, the oral adjuvant effect of LT was stated based on its capacity to induce serum and mucosal antibodies to the peptide antigens OVA and BSA. LT was not reported in combination with non-living microbial vaccines administered via the oral route at the time of this presentation, ie., LT had not been shown to induce specific, protective mucosal immunity to a pathogenic microorganism. (In this context, it should be noted that inappropriate antibody responses to pathogenic microorganisms can actually enhance their pathogenicity - a phenomenon known as "immune enhancement" and well documented in the disease dengue hemorrhagic fever. Therefore, the capacity of a substance to enhance antibody formation does not demonstrate that the substance will enhance protective immunity capable of assisting the host with clearance of the pathogen.) Nor had the differential toxicity of LT and CT been demonstrated in vivo. The material presented at the American Society for Microbiology Meeting in May of 1988 was subsequently published by Clements, et al., 1988, Vaccine 6:269–276; some of the data in the article regarding induction of immunity to peptides also appears in this Application as filed Jun. 2, 1989.

3. SUMMARY OF THE INVENTION

Accordingly, an object of this invention is an immunological adjuvant for peptide, polysaccharide or non-living microbial vaccines administered via the oral route.

Another object of the invention is a method for inducing protective (sometimes termed adaptive) immunity to pathologic antigens by multiple administrations of adjuvant with appropriate amounts of antigen.

An additional object of the invention is a pharmaceutical composition to induce a protective immune response to a pathogen using a peptide, polysaccharide or non-living microbial vaccine.

A further object of this invention is a pharmaceutical composition for stimulating protective immunity at mucosal surfaces throughout the host.

A further object of this invention is a pharmaceutical composition for stimulating long-lasting protective immunity of mucosal surfaces throughout the host.

A further object of this invention is a pharmaceutical composition for oral priming of the parenteral immune response.

Yet another object of the invention is an adjuvant having low toxicity at adjuvant-effective doses.

Still another object of the invention is the alteration of extant immunity manifested as allergic responses at mucosal surfaces, including the intestine and the respiratory tract.

These and additional objects of the invention are accomplished by the use of the heat-labile enterotoxin (LT) of *E. coli* as an immunological adjuvant for enhancing an animal's (host) immune response. In particular, LT potentiates the production of antigen-specific serum IgG and mucosal IgA as well as cellular immune responses following multiple administrations via the oral route simultaneously with antigen.

The antigen may consist of a peptide or polysaccharide component of a microorganism containing epitopes important in protective immunity to that microorganism, or of a non-living microorganism or extract of that microorganism containing epitopes essential for protective immunity to the microorganism. Alternatively, the antigen may consist of substances containing epitopes shared by substances (allergens) to which the host has previously established an atopic immune response (generally mediated by IgE antibodies) evoking allergic manifestations at mucosal surfaces.

It is apparent to someone who is skilled in the art that this invention will be useful for any specific antigen where a specific neutralizing antibody response would be useful in ablating the physiological or disease state associated with that antigen.

4. DESCRIPTION OF THE FIGURES

FIG. 1. Effect of LT on oral tolerance to OVA. Mice were primed orally with PBS, OVA, or OVA in combination with LT or LT-B at weekly intervals as indicated. Animals were boosted i.p. with OVA and serum anti-OVA IgG was determined by ELISA. Bars represent mean±SEM antibody response in each group 1 week after boost. Each group contained five to seven mice. Data for this Figure are presented in Table 1.

Figure 2:
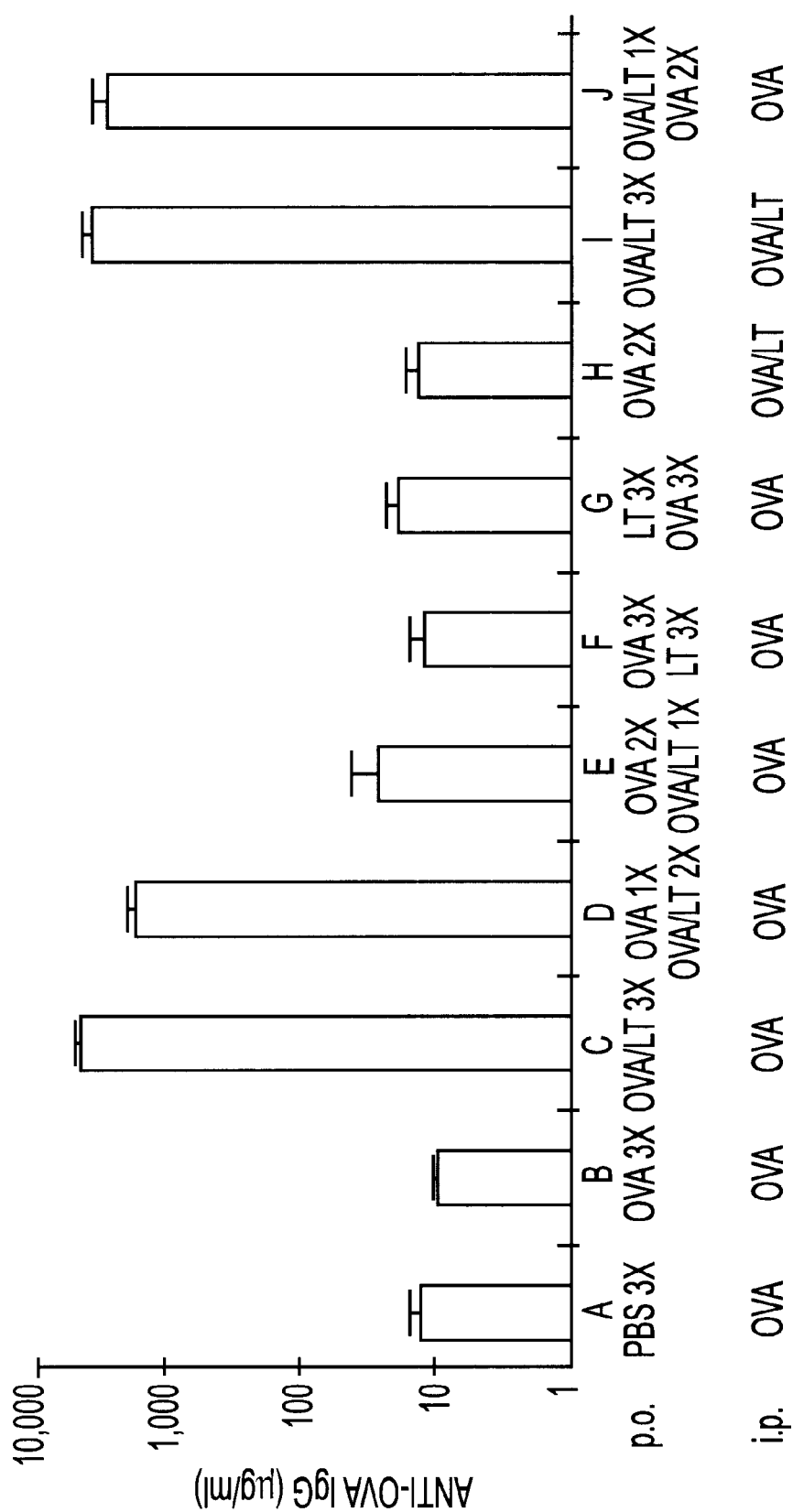

FIG. 2. Effect of varying the timing and route of delivery of LT on anti-OVA serum IgG response. Mice were primed orally with PBS, OVA, or OVA in combination with LT at weekly intervals as indicated. Animals were boosted i.p. with OVA or OVA in combination with LT and serum anti-OVA IgG was determined by ELISA. Bars represent mean±SEM antibody response in each group 1 week after boost. Each group contained five to seven mice. Data for this Figure are presented in Table 2.

Figure 3:
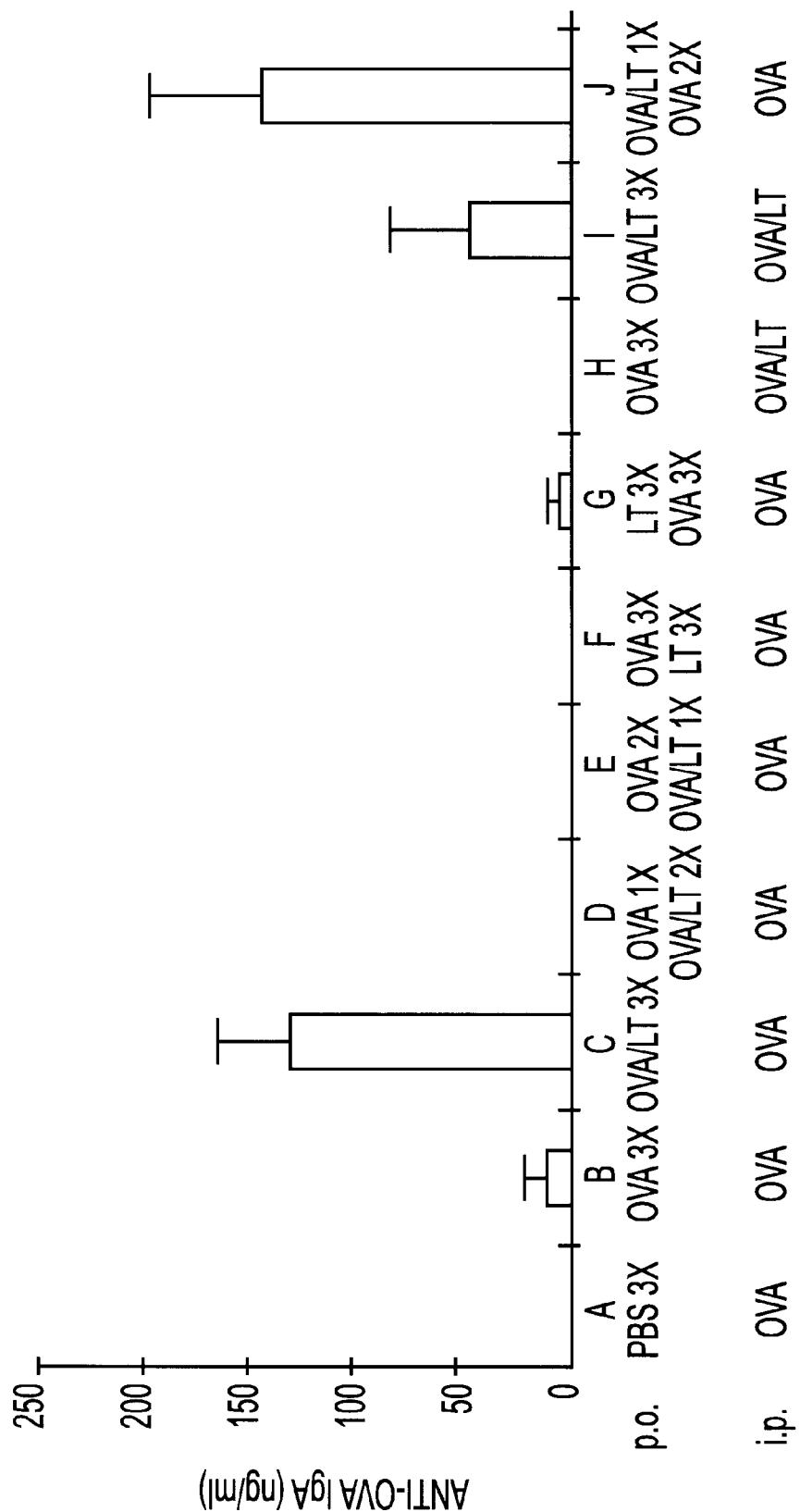

FIG. 3. Effect of varying the timing and route of delivery of LT on anti-OVA mucosal IgA response. Mice were primed orally with PBS, OVA, or OVA in combination with LT at weekly intervals as indicated. Animals were boosted i.p. with OVA or OVA in combination with LT and mucosal anti-OVA IgA was determined by ELISA. Bars represent mean±SEM antibody response in each group 1 week after boost. Each group contained five to seven mice. Data for this Figure are presented in Table 2.

Figure 4:
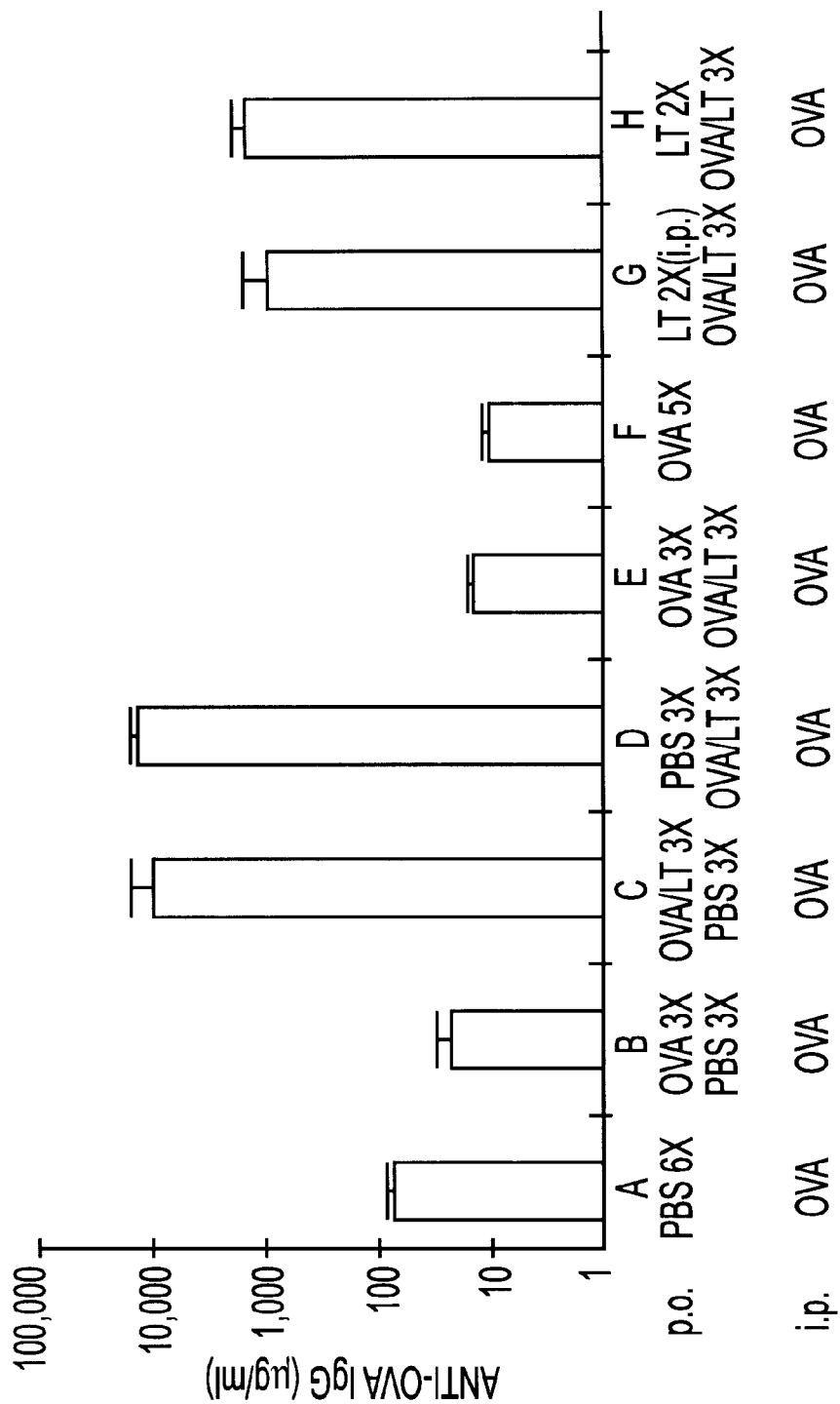

FIG. 4. Effect of prior exposure to OVA on the ability of LT to influence anti-OVA serum IgG response. Mice were primed orally with PBS, OVA, or OVA in combination with LT at weekly intervals as indicated. Animals were boosted i.p. with OVA and serum anti-OVA IgG was determined by ELISA. Bars represent mean±SEM antibody response in each group 1 week after boost. Each group contained five to eleven mice. Data for this Figure are presented in Table 3.

FIG. 5. Effect of prior exposure to OVA on the ability of LT to influence anti-OVA mucosal IgA response. Mice were primed orally with PBS, OVA, or OVA in combination with LT at weekly intervals as indicated. Animals were boosted i.p. with OVA and mucosal anti-OVA IgA was determined by ELISA. Bars represent mean±SEM antibody response in each group 1 week after boost. Each group contained five to eleven mice. Data for this Figure are presented in Table 3.

Figure 6A:
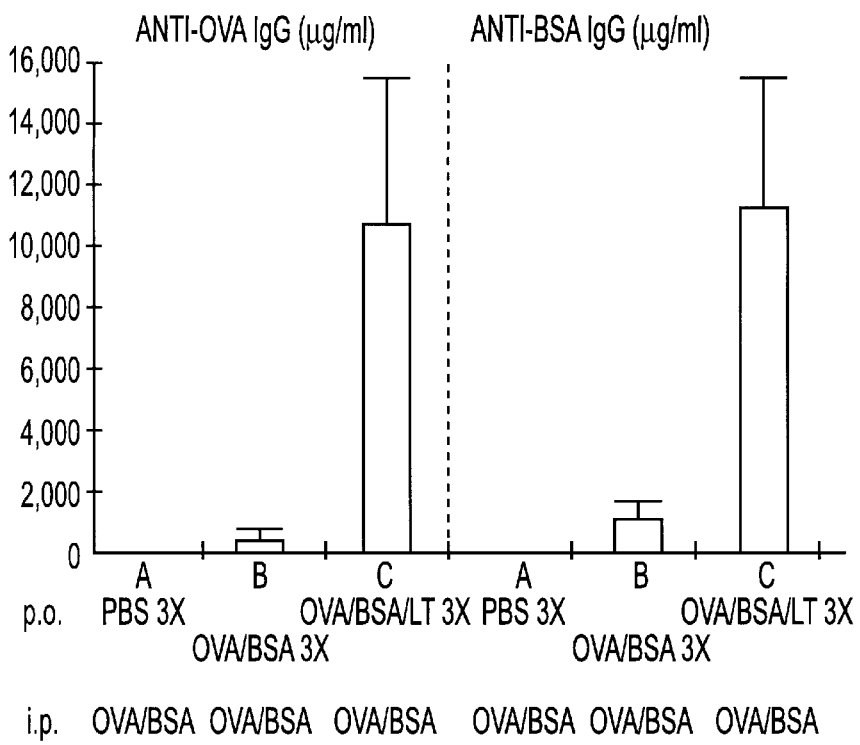
Figure 6B:
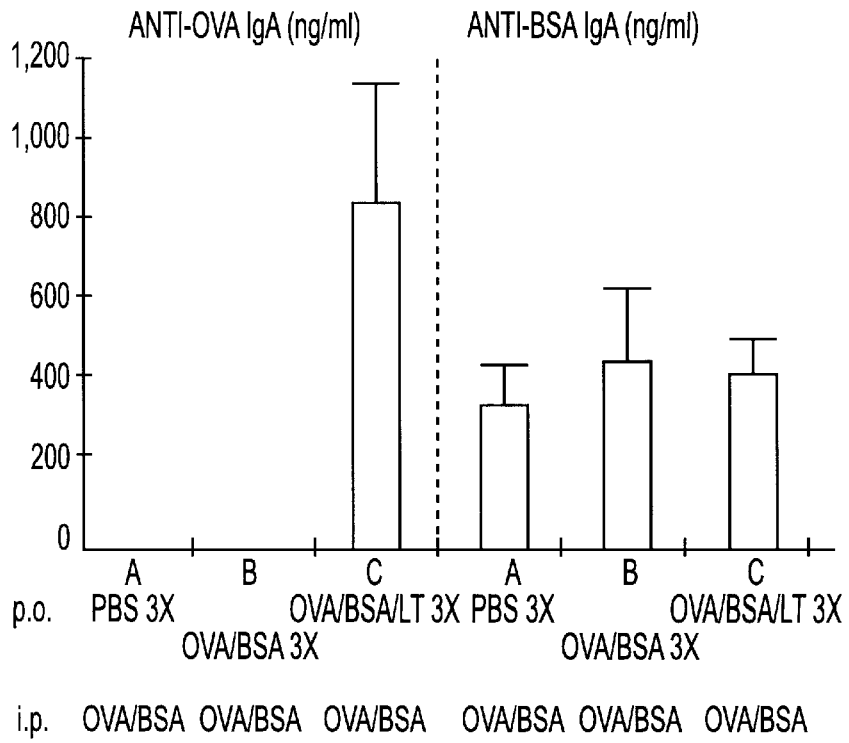

FIG. 6. Use of LT as an adjuvant with two unrelated antigens. Mice were primed orally with PBS, OVA and BSA, or OVA and BSA in combination with LT at weekly intervals as indicated. Animals were boosted i.p. with OVA and BSA and serum anti-OVA IgG (upper left panel), serum anti-BSA IgG (upper right panel), mucosal anti-OVA IgA (lower left panel), and mucosal anti-BSA IgA (lower right panel) were determined by ELISA. Bars represent mean±SEM antibody response in each group 1 week after boost. Each group contained six to ten mice. Data for this Figure are presented in Table 4.

FIG. 7. Effect of route of immunization on anti-OVA responses. Mice were primed orally with OVA in combination with LT at weekly intervals as indicated.

Animals were boosted i.p., i.m., or s.c. with OVA or not boosted, and mucosal anti-OVA IgG and IgA were determined by ELISA. Bars represent mean±SEM antibody response in each group 1 week after boost. Each group contained five to six mice. Data for this Figure are presented in Table 5.

Figure 8B:
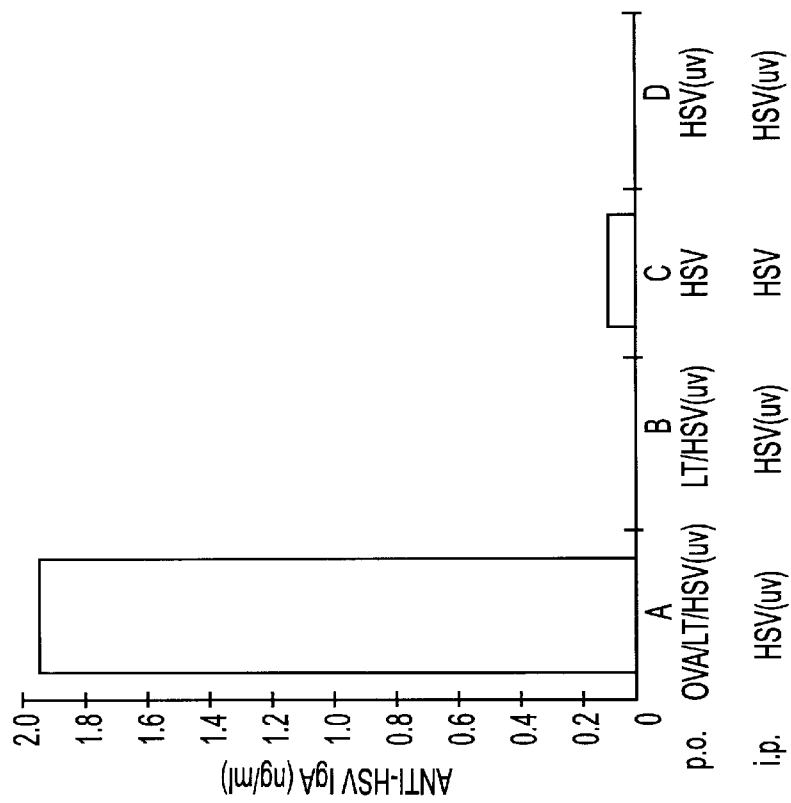
Figure 8A:
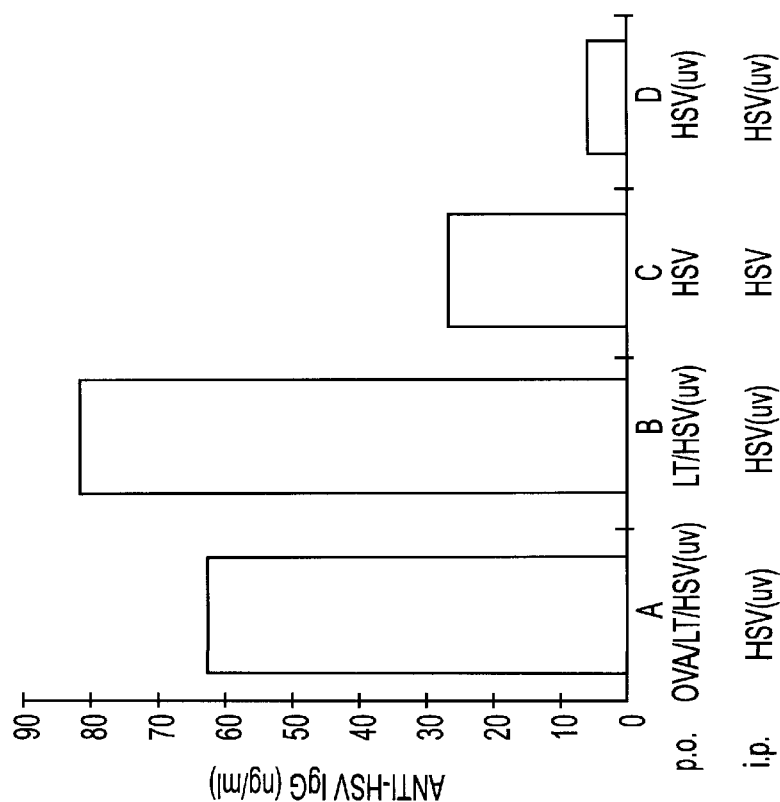

FIG. 8. Use of LT as an adjuvant with Herpes simplex virus. Mice were primed orally as follows: On day 0, Group A received 0.5 ml of PBS containing 5 mg of OVA, 20 μg of u-v inactivated Herpes simples virus type 1 [HSV(uv)], and 25 μg of LT; Group B received 0.5 ml of PBS containing 20 μg of HSV(uv) and 25 μg of LT; Group C received 0.5 ml of PBS containing 20 μpg of viable HSV; and Group D received 0.5 ml of PBS containing 20 Mg of HSV(uv). This regimen was repeated on days 7 and 14. On day 21, animals were boosted i.p. with 0.5 ml of PBS containing 1 μg of HSV(uv) in 20% Maalox. Serum IgG and mucosal IgA responses were determined one week later for HSV by ELISA using microtiter plates precoated with 10 μg per well of HSV(uv). Each group contained seven to nine mice.

Figure 9:
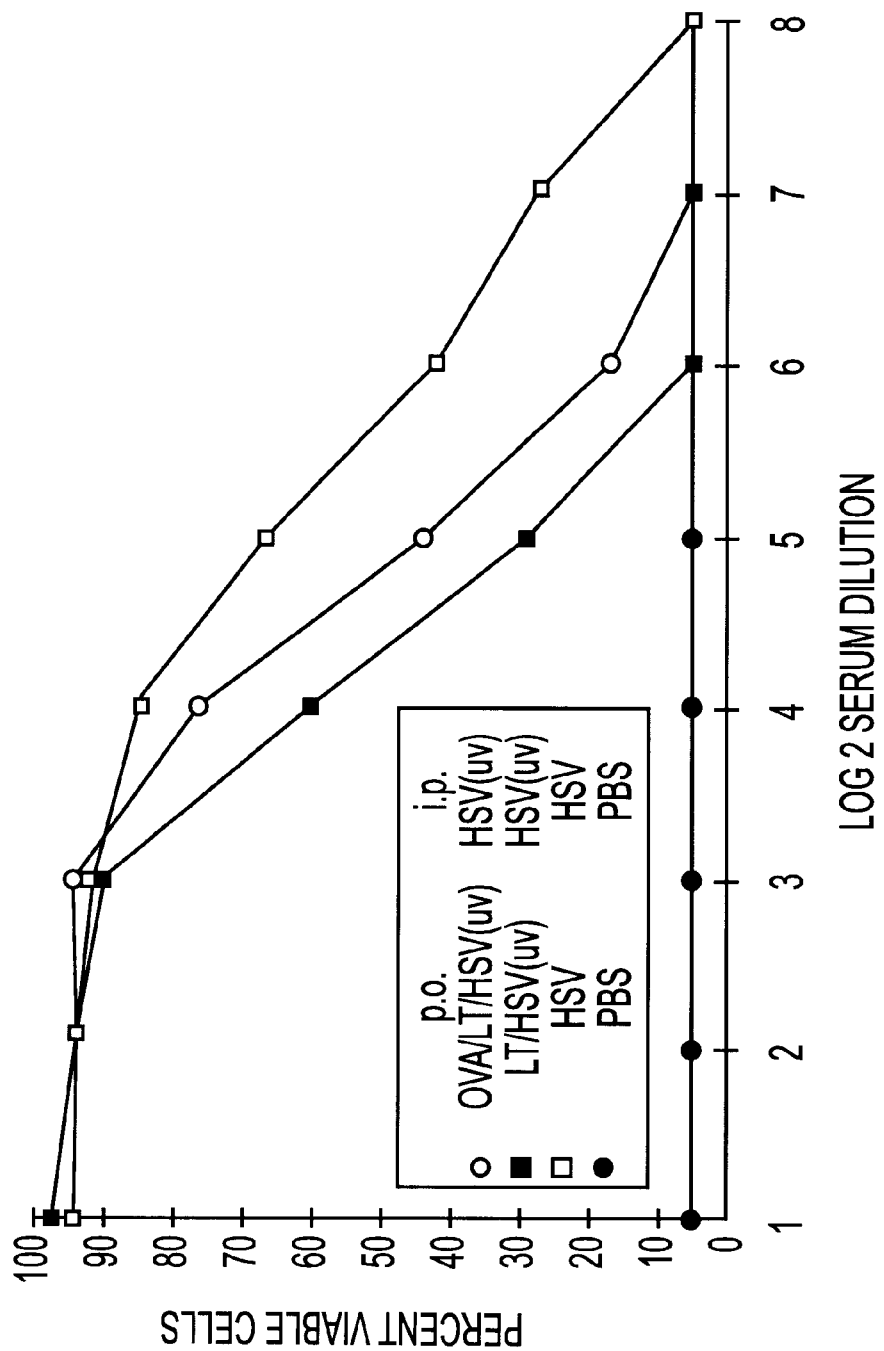

FIG. 9. Neutralization of HSV-1 by antiserum against orally administered, u-v inactivated HSV-1. Sera from mice which had been immunized with u-v inactivated HSV-1 were added to aliquots of HSV-1. The mixtures were then used to infect monolayers of African Green Monkey Kidney (AGMK) cells. Cells were challenged with virus at a multiplicity of infection of 10 pfu per cell or mock infected in the presence of the mouse serum. After 18 hr, the ability of the mouse sera to neutralize HSV-1 infectivity was quantitated by counting the number of cells in each well which were rounded or spindle-shaped, the typical cytopathic effect (CPE) induced by HSV-1.

Figure 10:
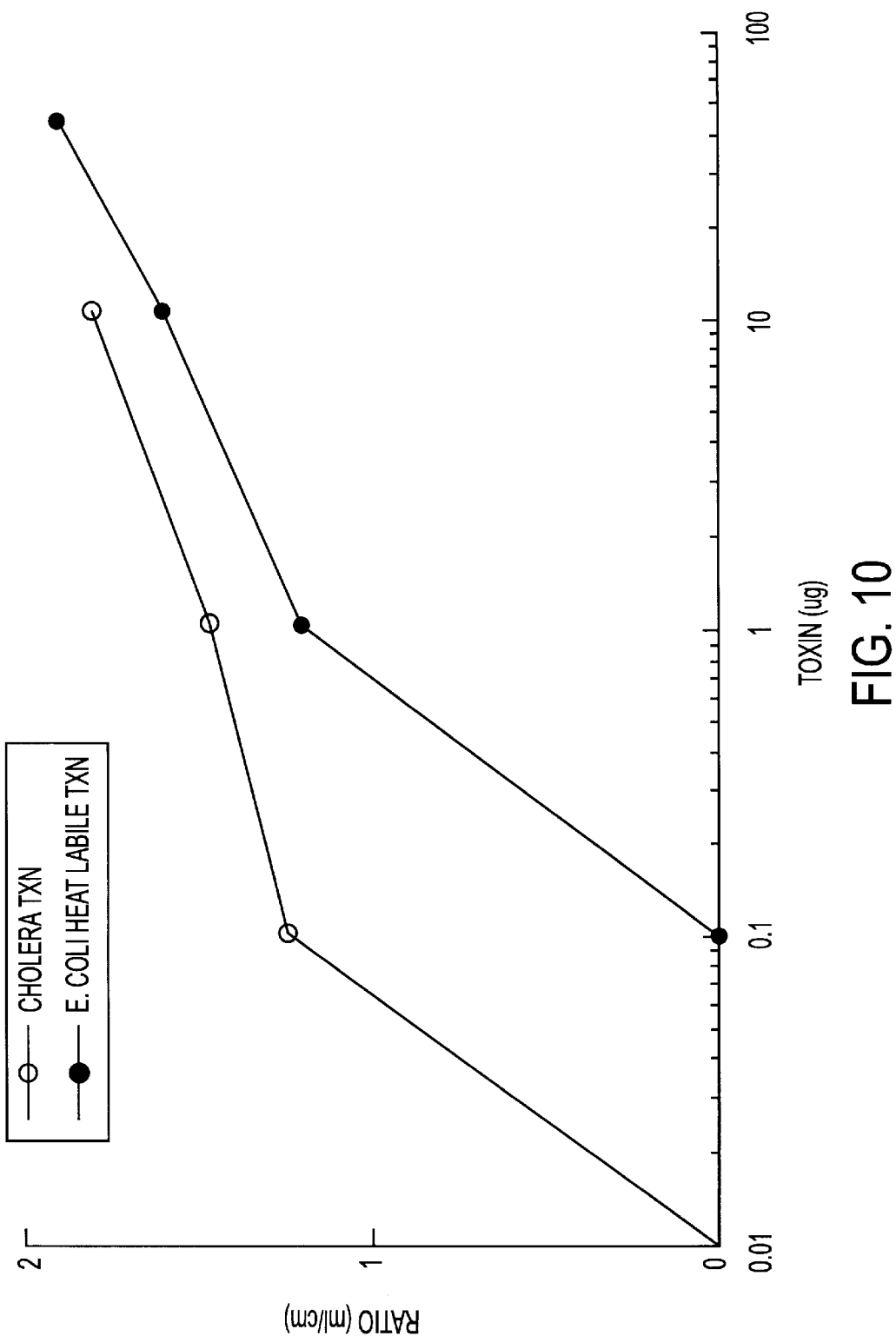

FIG. 10. A graph demonstrating differences in toxicity between LT and CT in vivo as demonstrated by fluid accumulation within rabbit intestinal (ileal) loops at 18 hrs post-inoculation.

Figure 11:
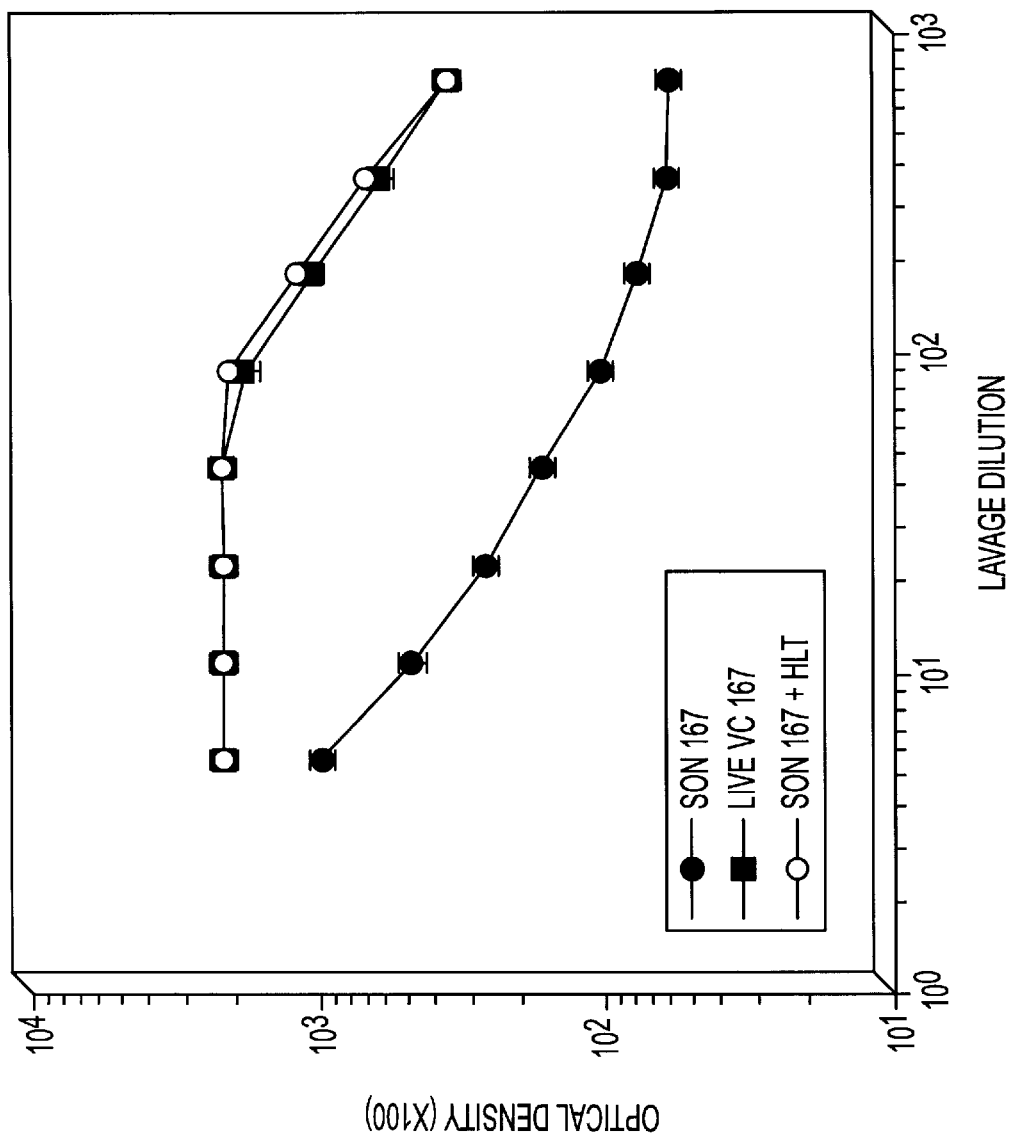

FIG. 11. A graph showing the intestinal IgA response to oral killed *Campylohacter coli* with/without LT adjuvant compared to oral live bacteria.

Figure 12:
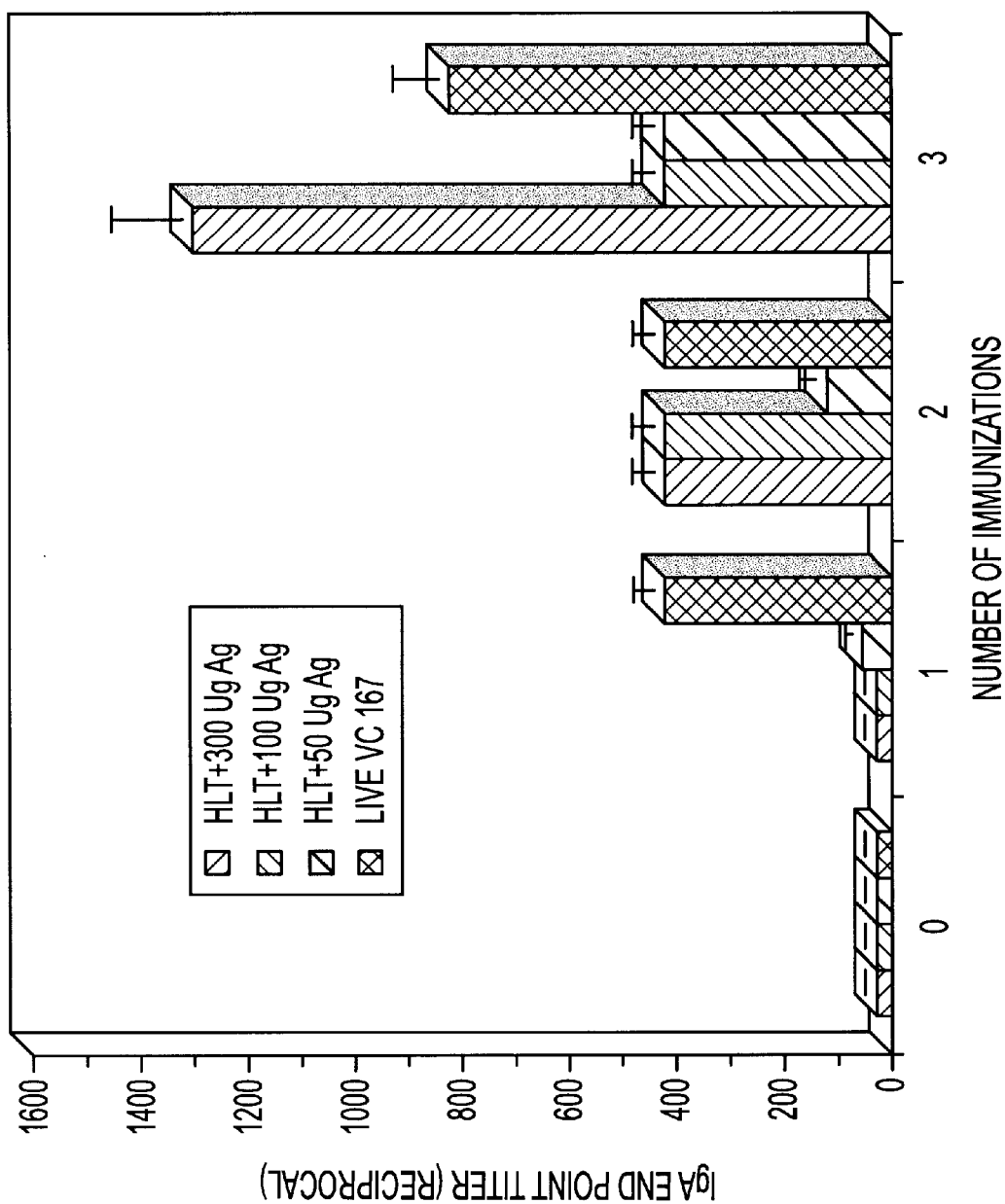

FIG. 12. A graph showing intestinal IgA responses to various oral doses of *C. coli*, strain VC 167, live or killed by sonication and combined with 25 μg LT.

Figure 13:
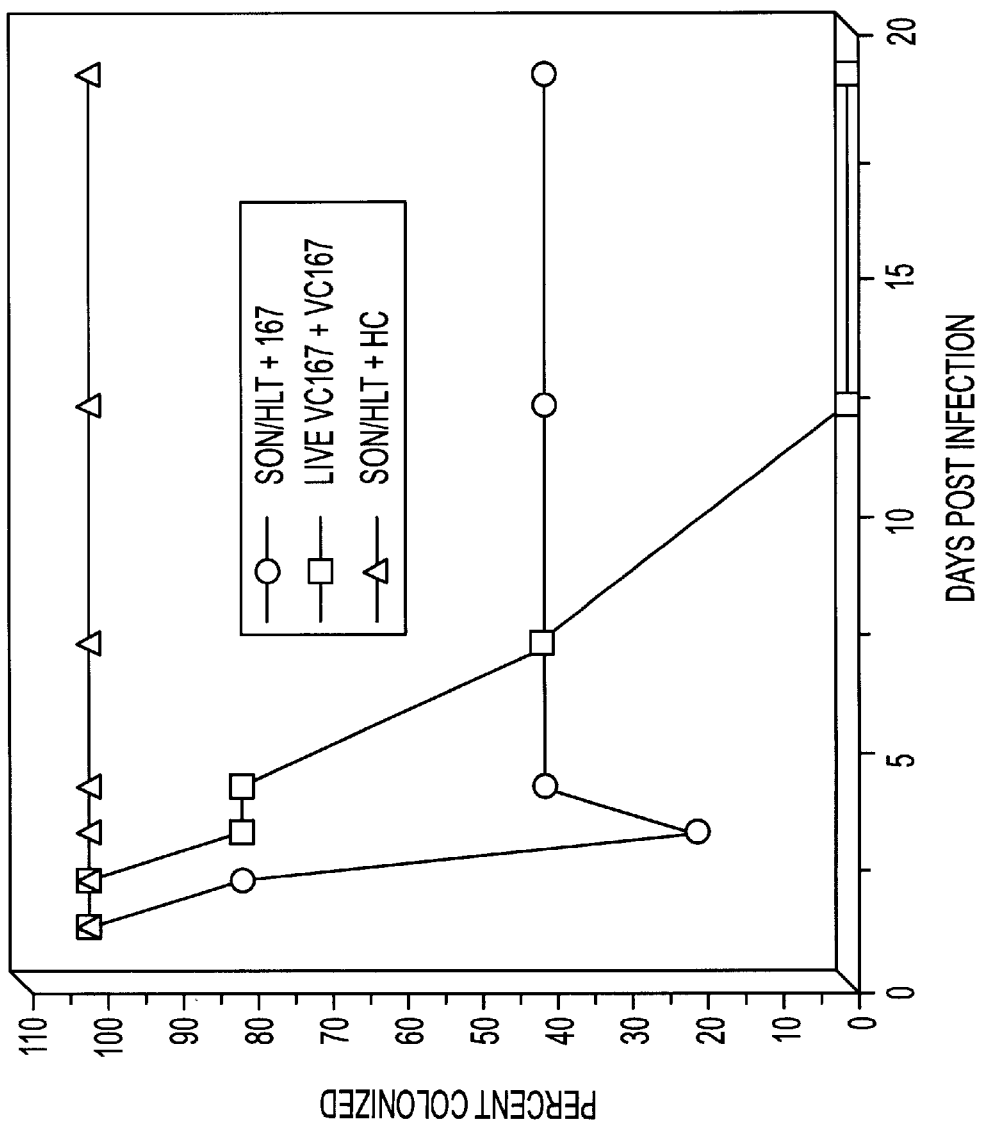

FIG. 13. A graph demonstrating protective immunity (resistance to bacterial colonization) induced by three weekly oral administrations of *C. coli* killed by sonication and combined with 25 μg LT.

Figure 14:
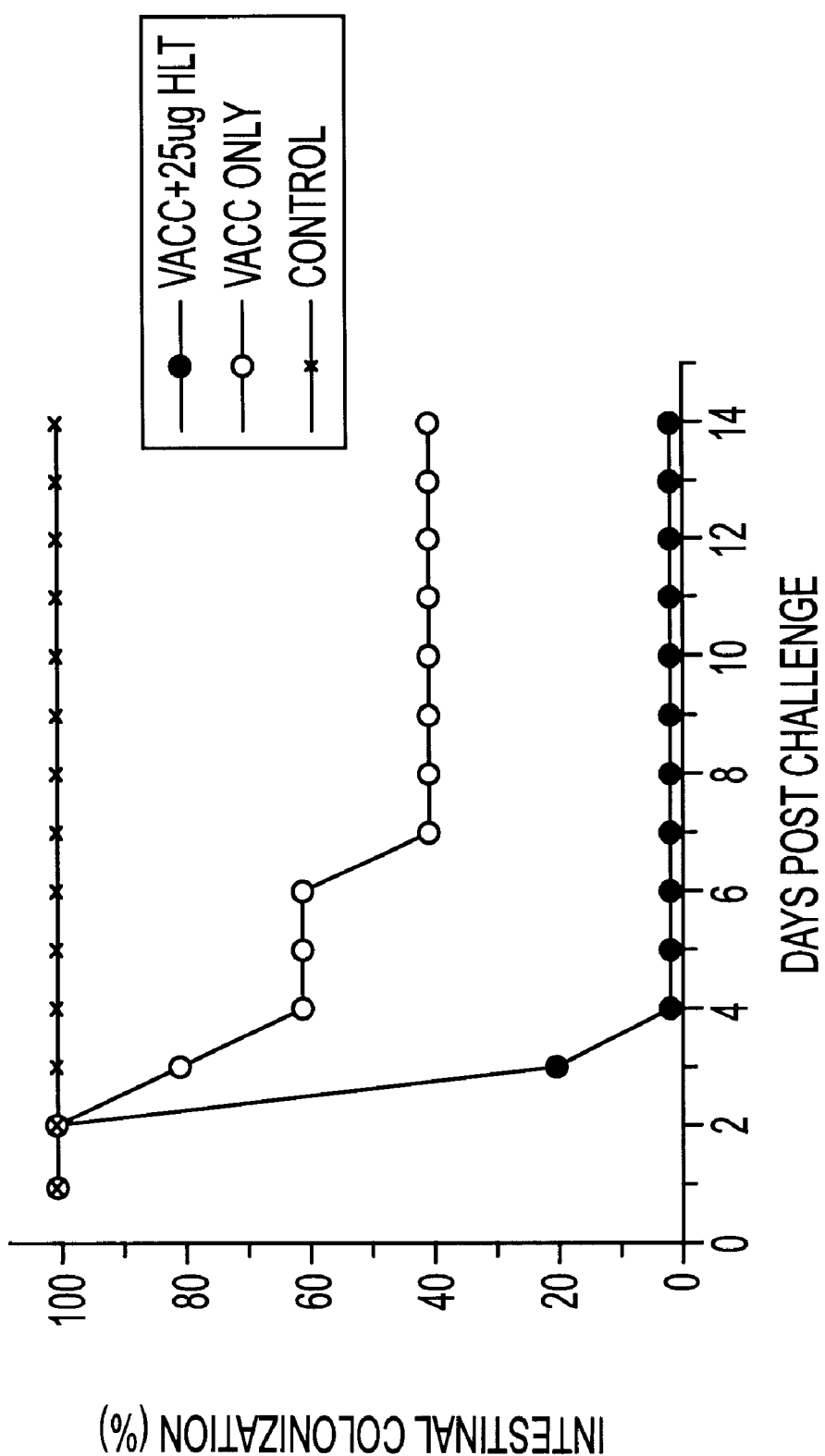

FIG. 14. A graph demonstrating protective immunity (resistance to bacterial colonization) induced by 3 oral administrations at 48 hr intervals of killed *C. jejuni* with/without 25 μg LT.

Figure 15:
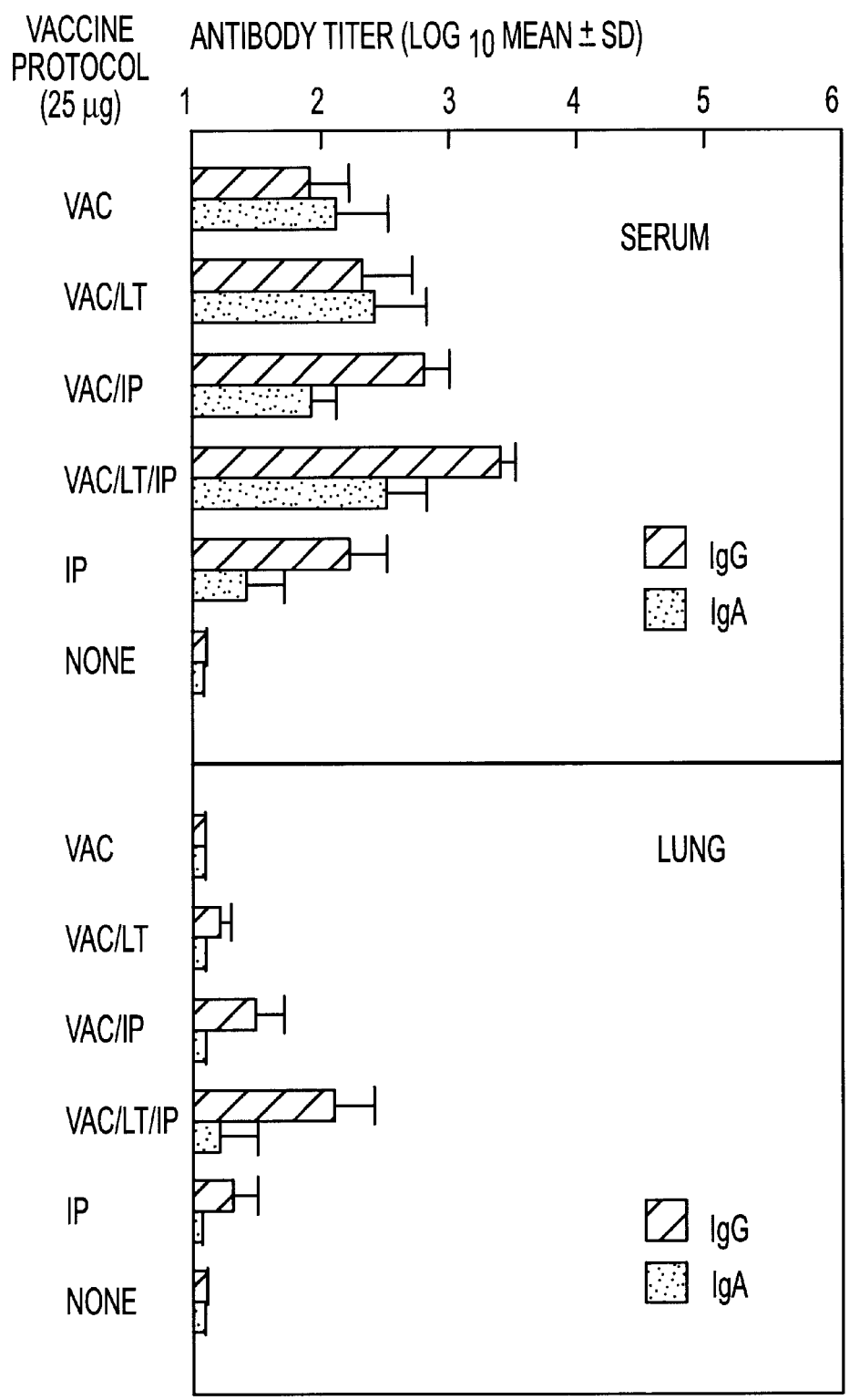

FIG. 15. A graph demonstrating persistence of both IgG and IgA antibody to influenza virus in the serum and in the lung 3 months following completion of oral immunization with 3 weekly administrations of 25 μg of LT combined with formalinized influenza vaccine and a parenteral (intraperitoneal) boost with vaccine alone.

5. DETAILED DESCRIPTION OF THE INVENTION

Experimental evidence presented herein shows that LT has the effect of preventing development of tolerance to antigens administered orally in conjunction with LT. However, it is not the ability of LT to influence the induction and maintenance of oral tolerance that makes it useful for prevention of infectious diseases. LT has also shown utility as an adjuvant for orally administered microbial vaccines; such administration results in the production of antigen-specific serum IgG and mucosal IgA as well as cellular immune responses that singly, or combined, result in enhanced resistance to subsequent microbial challenge (protective immunity).

As a first embodiment of the present invention is a pharmaceutical composition and a method for enhancing the host's immune response to any novel antigen co-administered with LT by the oral route at least 2 times separated in time by at least 48 hours. A quantity of between 1 and 50 μg of *Escherichia coli* LT (purified according to Clements and Finkelstein, 1979, Infect. Immun. 24:760–769) is administered by oral ingestion in combination with an effective dose of the desired antigen, both contained in a suitable pharmaceutical carrier. In a preferred embodiment, this pharmaceutical composition is prepared in combination with a buffer, such as 5% sodium bicarbonate, to neutralize stomach acid and minimize degradation.

The dose of LT, because of its route of administration, is not proportioned with respect to the weight of the recipient species hut instead is proportioned with respect to the relative responsiveness of the species. For instance, it has been observed that the same dose of LT that is effective in the mouse is also suitable for rabbits weighing 70 times as much. A dose of LT of only 5 μg appears effective at stimulating IgA production in monkeys weighing nearly 500 times more than a mouse. Previous exposure to LT, which induces vigorous immunity to itself when administered orally, does not obviate its effectiveness as an adjuvant.

The present invention also provides a pharmaceutical composition for inducing protective immunity to a given vaccine, either peptide, polysaccharide or non-living whole microorganism or extract thereof, eliminating the need for the live, replicating organisms (which are potentially infectious and thus capable of causing disease) normally required for induction of persistent protective immunity.

Further, the invention provides a pharmaceutical composition that efficiently stimulates mucosal immunity, i.e., immunity at the portal of entry for most common pathogens. Examples of important pathogens acquired via mucosal surfaces are air-borne pathogens (such as influenza virus, measles virus), food- and water-borne pathogens (such as cholera bacteria, rotavirus) and sexually-transmitted pathogens (such as gonorrhea bacteria or human immunodeficiency virus).

Importantly, LT fails to abrogate established tolerance such as would exist in healthy individuals to dietary antigens; this implies that the LT-immunized host will not be stimulated to produce immune responses to a host's intestinal food contents when given LT by the oral route. Also of importance with respect to the utility of this invention is the observation that mucosal immunity stimulated by oral exposure to antigen adjuvanted by LT is not limited to the intestine. Immunologists have established that mucosal immunity "spreads" to all mucosal surfaces of the body, such as the lung, by "homing" to (cross-seeding) unexposed mucosal surfaces by specialized mucosal immune cells reactive with antigen. Similar mechanisms, when stimulated with the appropriate antigen, may allow immune clearance of allergenic substances from mucosal surfaces while competing for, and thus minimizing, the antigen binding of the IgE that mediates the allergic response. Immunological blockade of such allergic responses by oral immunization with LT adjuvant comprises another embodiment of the present invention.

Further, the invention provides a pharmaceutical composition that induces long-lasting immunity (both mucosal and systemic) by stimulating thymus-derived (T) lymphocytes responsible for immunological memory.

Further, the invention provides a pharmaceutical composition that by stimulating T lymphocytes, particularly cytolytic T cells, induces a class of cellular immunity critical for protection against intracellular pathogens such as certain bacteria (Salmonella species, Listeria species, Mycohactelia species as examples), most viruses, certain parasites (Toxoplast?ma species as an example) and fungi (Pneumocystis species as an example). Pathogens that require T cell-mediated immunity (also termed cellular immunity) for their immune clearance comprise the majority of life-threatening infective agents. Such immunity is generally not induced in the absence of a live, replicating (and potentially pathogenic) antigen. The inability of conventional killed vaccines (adjuvanted by alum salts and administered parenterally) to induce either cellular immunity or mucosal immunity is the basis for the frequent ineffectiveness of such vaccines at producing long-lasting protective immunity. Classic examples are the standard killed vaccines used for influenza and cholera, which exhibit a window of protection as short as 6 weeks (largely due to a spill-over of serum IgG onto mucosal surfaces), and measles vaccine, the use of which has lead to measles epidemics in college students immunized as young children but no longer protected as young adults.

Further, the invention provides a pharmaceutical composition that primes the host for subsequent rapid development of systemic (parenteral) immunity once the host receives a parenteral challenge with the microorganism, such as would occur with mosquito-borne malaria parasites or syringe-inoculated HIV.

Described in this application are examples of non-living microbial antigens to which protective immune responses are induced by the present invention. These examples are the viruses herpes simplex virus type 1 and influenza in the mouse and pathogenic species of the bacterium *Campylobacter* coli in the mouse, the rabbit and the monkey. The data provided indicate the utility of LT as an adjuvant for the induction of protective immune responses.

Described in this application is the ability of heat-labile enterotoxin (LT) of *E. coli* to influence the induction and maintenance of tolerance in animals primed orally with a soluble protein antigen, or in animals primed orally with two unrelated protein antigens administered simultaneously. The initial observations in this property of LT were made in connection with administration of LT to animals primed orally with ovalbumin (OVA), or with ovalbumin and bovine serum albumin (BSA). Simultaneous administration of an effective amount of LT with OVA was shown to prevent the induction of tolerance to OVA and to increase the serum anti-OVA IgG response 30 to 90 fold over phosphate buffered saline (PBS) primed and OVA primed animals, respectively. This effect was determined to be a function of the enzymatically active A subunit of the toxin since the B (binding) subunit alone was unable to influence tolerance induction, and probably reflects the ADP-ribosylating activity of the subunit and subsequent intracellular increase in cAMP.

According to one embodiment of the present invention, an effective amount of LT is able to influence the induction and maintenance of tolerance. To demonstrate this property, this method was examined in a murine model where animals were primed orally with a soluble protein antigen, OVA or in animals primed orally with two unrelated protein antigens, OVA and BSA, administered simultaneously.

Simultaneous administration of an effective amount of LT with OVA prevents the induction of tolerance.

Another embodiment of the present invention is the adjuvant property of LT for peptide antigens that are weakly immunogenic. Administration of an effective amount of LT simultaneously with OVA was shown to increase the anti-OVA IgG response 30 to 90 fold over PBS primed and OVA primed animals, respectively. In addition, serum IgG and mucosal IgA responses in animals receiving an effective amount of LT on only one occasion, that being on first exposure to antigen, were equivalent to responses after three OVA/LT primes indicating that commitment to responsiveness occurs early and upon first exposure to antigen. This application also presents data that demonstrates that the direction of the response to either predominantly serum IgG or mucosal IgA may be controlled by whether or not a parenteral booster dose is administered. Thus appropriate antibody responses against pathogens which colonize or invade across a mucosal surface can be directed to that surface, while a significant serum antibody response can be developed to prevent infection by pathogens against which serum antibody is protective.

5.1. GENERAL DESCRIPTION OF SOURCE OF LT FOR COMPOSITION

The LT toxin is encoded by a naturally occurring plasmid which is found in all enterotoxigenic *E. coli*. Thus, the holotoxin can be readily isolated from any such *E. coli* strain, many of which are publicly available. This plasmid is also freely transmissible, particularly between strains of the Enterobacteriaceae. Therefore, transformed strains of other microorganisms which have acquired the necessary plasmid are also easily created. Accordingly, the LT toxin proposed for use in the present invention may be isolated either from the native *E. coli* strains, or from microbial strains which express the gene encoding the LT toxin. A method of isolation of the LT holotoxin has been described by Clements and Finkelstein (1979, Infect. Immun. 29: 91–97). Alternate methods of purification will be apparent to those skilled in the art.

5.2. MODE OF ADMINISTRATION OF LT AND UNRELATED ANTIGENS

In accordance with the disclosed utility of the LT toxin, LT can be administered in conjunction with any biologically relevant antigen. In a preferred embodiment, the LT and antigen are administered simultaneously in a pharmaceutical composition comprising an effective amount of LT and an effective amount of antigen. The mode of administration is oral. The respective amounts of LT and antigen will vary depending upon the identity of the antigen employed and the species of animal to be immunized. Adjustment and manipulation of established dosage ranges used with traditional carrier conjugates, for adaptation to the present therepeutic composition, is well within the ability of the skilled artisan.

For example, a typical dosage of the combination of LT and antigen for a rodent is 15–50 μg of LT and 0.5 to 5 mg of antigen delivered orally. In one embodiment, the initial administration of LT and antigen is followed by a boost of the relevant antigen. The timing of boosting may vary, depending upon the antigen and the species being treated. The modifications in dosage range and timing of boosting for any given species and antigen is readily determinable by routine experimentation. The boost may be of the antigen alone, or in combination with LT. The mode of administration may be either oral or parenteral; however, if LT is used in the boost, administration should be oral.

The method and compositions of the present invention are intended for use in both immature and mature vertebrates, in particular birds, mammals, and humans. Those conditions for which effective prevention may be achieved by the present method will be obvious to the skilled artisan upon reading of the present disclosure, (some of which have been indicated below). Also, the use of the present methods and compositions is not limited to prophylactic application; there are therapeutic applications for the LT in combination with the relevant antigen as well.

5.3. THERAPEUTIC AND PROPHYLACTIC APPLICATION

The adjuvant properties of LT make it useful in prophylactic compositions for prevention of microbial diseases, i.e., conditions caused by bacterial, viral, fungal, protozoan or helminthic pathogens.

By way of example, some of the useful antigens would include antigens from pathogenic strains of bacteria (*Streptococcus pyogenes, Neisseria gonorrheae, Corynebacterium diphtheriae, Clostridium botulinum, Clostridium perfringens, Clostridium tetani, Hemophilus influenza, Klebsiella pneumoniae, Klebsiella ozaenae, Klebsiella rhinoscleromotis, Staphlococcus aureus, Vibro cholerae, Escherichia coli, Pseudomonas aeruginosa, Campylobacter (Vibrio) fetus) Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma, Rickettsia prowazeki, Rickettsia tsutsugumushi*, Chlamydia); pathogenic fungi (*Coccidioides immitis, Aspergillus fumigatus, Candida albicans, Blastomyces dermatitidis, Cryptococcus neoformans, Histoplasma immitis*); protozoa (*Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Plasmodium vivax, Plasmodium falciparum, Plasmodium malaria*); Helminths (*Enterobius vermicularis, Trichuris trichiura, Ascaris lumbricoides, hookworms, Trichinella spiralis, Strongyloides stercoralis, Schistosoma japonicum, Schistosoma mansoni, Schistosoma haematobium*); pathogenic viruses (Poxviruses; Herpesviruses, Adenovinises, Papovaviruses, Enteroviruses, influenza viruses, parainfluenza viruses, mumps, measels, respiratory syncytial virus, rubella, arboviruses, rhabdoviruses, arenaviruses, Hepatitis, rhinoviruses, coronaviruses, reoviruses, rotoviruses, human immunodeficiency viruses.

As noted previous, both CT and LT have been reported to possess adjuvant activity. However, LT has important differences from CT with respect to toxicity in vivo. Data (Table 6) establish a dose of LT and mode of administration (3 oral administrations with killed bacterial antigen plus bicarbonate [to neutralize stomach acid] at 48 hr intervals) shown to induce protective campylobacter immunity in the rabbit without the toxic manifestations that would be seen with comparable doses of CT.

TABLE 6

Adjuvant Admministered With Campylobacter Antigen Confers Protection Against Subsequent Challenge

| Rabbits immunized with | Rabbits challenged with[1] | Colonization (days + S.D.) | Number resistant[2] |
|---|---|---|---|
| — | VC167 | 8.1 + 1.2 | 0/6 |
| 3 (OA) | VC167 | 8.0 + 1.0 | 0/7 |
| 3 (SON)[3] | VC167 | 7.0 + 1.0 | 1/8 |
| 3 (SON + OA) | VC167 | 2.7 + 2.4 | 9/11 |
| 3 (SON) + 1 (OA) | VC167 | 8.0 + 0.8 | 0/4 |
| — | 81116 | 7.6 + 0.6 | 1/3 |
| 3 (SON + OA) | 81116 | 6.0 + 1.0 | 1/4 |

[1]VC167 is a Lior 8 strain of C. coli and 81116 is a Lior 6 strain of C. jejuni
[2]Number of animals negative for Campylobacter 5 days after RITARD challenge/total number in group
[3]Sonicates (SON) used for immunization were prepared from VC167

Data rabbit ileal loops (FIG. 10) demonstrate that LT is 10-fold less toxic in vivo than CT.

As demonstrated elsewhere in this application, LT is unable to abrogate tolerance, unlike CT. This difference is important in the context of the utility of LT as as an oral adjuvant in that LT is less likely to induce "bystander" immunity to intestinal food contents but instead is adjuvant activity will be limited to the novel antigens presesnted with it.

LT shares the basic geometry (1 A chain, 5 B chains) and approximately 80% amino acid homology with CT. LT also shares toxic mechanisms and one cellular ligand (GM, ganglioside) with CT. The toxic mechanisms may be relevant to the adjuvant action of both substances (Lycke et al., 1992, Eur. J. Immunol. 22:2277–2281), but LT is distinct from CT in terms of a number of physical properties (Clements, et al., 1980, Infect. Immun. 29:91–97) and biologically in the following ways:

a) Biodistribution: It is well established that LT and CT both bind to the ganglioside $G_{M1}$, which while broadly distributed, is concentrated in the intestine where their toxic action is manifested. However, as a result of its structural differences, LT also binds to a ligand distinct from $G_{M1}$, i.e., galactose (Clements, ibid.), a sugar that is widely distributed on the surface of all cells of the body as well as in mucous. Galactose is a component of $G_{M1}$ as well, and may represent the binding site for LT on $G_{M1}$. The affinity of LT for galactose implies that when LT is administered by oral ingestion it distributes more broadly than CT to all surfaces that it comes in contact with from the mouth to the intestine (unlike the situation when the infective *E. coli* "delivers" LT to the intestine). These surfaces include extensive mucosal immune system tissue in the pharynx and trachea that may be immune system targets of LT but are less likely to be targets of CT.

Another implication of this ligand affinity is that orally-administered LT, by being more broadly distributed on upper GI surfaces, is less concentrated in the intestine where it functions as a toxin. This may be one reason (but not the only reason—see below) that LT is less toxic than CT in vivo.

b) Toxic State at Time of Production: Another critical biological difference between LT and CT is that CT is secreted from its host organism while LT is retained within its host organism. Both LT and CT must be proteolytically cleaved at a specific site on the A chain in order to express their toxic action. Because CT is secreted by its host organism into an environment rich in proteolytic enzymes, it is cleaved immediately and expresses its toxicity immediately. LT, on the other hand, must be extracted from its host organism. This can be done under conditions that minimize its proteolytic cleavage (Clements and Finkelstein, 1979, Infect. Immun. 24:760–769) and thus prevent it from achieving a toxic state. After oral ingestion, conversion of LT to a toxic state occurs in the proteolytic environment of the mammalian stomach and intestine, but this process is incremental over time and thus delayed relative to CT.

In summary, LT differs from CT in terms of its theoretical biodistribution and its relative toxicity in vivo at the time of its administration. These differences allow oral administration of LT at adjuvant-effective doses that are not overtly toxic—a critical practical distinction from CT. On the basis of animal studies, it is anticipated that the adjuvant-active oral dose range in the human will be between 5 $\mu$g and 25 $\mu$g per individual; these same doses manifest no toxicity in the rabbit or the mouse, and 5 $\mu$g appears adjuvant-active in the monkey (Table 11). CT has been administered orally to humans and found to be overtly toxic (diarrheagenic) at a dose of 5 $\mu$g and at a dose of 25 $\mu$g CT induces a 20 L (potentially lethal) intestinal purge (Levine, et al., 1983, Microbiol. Rev. 47:510–550). While LT has yet to be tested directly in humans, it is anticipated on the basis of the rabbit studies (note that with many other microbial toxins, particularly Gram-negative endotoxins, that the rabbit and the human display similar toxic sensitivities) that LT will be well tolerated in the 5–25 $\mu$g dose range. On the basis of the data in FIG. 10, it is possible that greater than 250 $\mu$g of LT will be required to manifest toxicity in the human, which provides a substantial window of safety.

6. EXAMPLES
6.1. PURIFICATION OF CT, LT, AND LT-B

CT was prepared as described by Mekalanos et al. (1978). The culture conditions and purification of LT and LT-B were as previously described (Clements and Finkelstein, 1979; Clements and El-Morshidy, 1984). Organisms were cultured overnight at 37° C. with vigorous aeration and agitation after inoculation with $10_6$ viable bacteria per ml. The bacteria were harvested by centrifugation at 4° C., and the cells were suspended in TEAN buffer (0.05 M Tris, 0.001 M EDTA, 0.003 M $NaN_3$, 0.2 M NaCl, pH 7.5) and lysed by French pressure cell. The crude lysate was then dialyzed against TEAN buffer and, after centrifugation, applied directly to columns of Sepharose 4B (Sigma Chemical Co., St. Louis, Mo.) equilibrated with TEAN buffer. LT or LT-B was then eluted from the columns with 0.2 M galactose in TEAN. Purified LT and LT-B were examined and found to be free of contaminating endotoxin with the Limulus Amebocyte Lysate Assay (Sigma Chemical Co.).

6.2. IMMUNIZATION

The procedures for immunization were essentially the same as those described by Elson and Ealding (1984b) for studying the influence of CT on induction of oral tolerance. Ovalbumin for immunization was Calbiochem 5X crystalline egg albumin (Behring Diagnostics, La Jolla, Calif.). Bovine Serum Albumin for immunization was Fraction V, RIA grade (United States Biochemical Corporation, Cleveland, Ohio). Animals were inoculated intragastrically with a blunt tipped feeding needle (Popper & Sons, Inc., New Hyde Park, N.Y. Oral inoculations consisted of 0.5 ml of PBS (0.01 M $Na_2HPO_4$, 0.003 M $KH_2PO_4$, 0.1 M NaCl, pH 7.2), 0.5 ml of PBS containing 5 mg of OVA, or 0.5 ml of PBS containing 5 mg of OVA and 25 $\mu$g of LT. For some experiments, LT was replaced with 25 $\mu$g of CT or with an equimolar amount of LT-B (17 $\mu$g); for others, BSA was included with the OVA. Following the oral inoculations, animals were boosted i.p. with 1 $\mu$g of OVA in 20% Maalox (William H. Rorer, Inc., Washington, Pa.) or, where indicated, with 1 $\mu$g of OVA in combination with 1 $\mu$g of BSA or 25 $\mu$g of LT in 20% Maalox. One week after the i.p. inoculation animals were sacrificed and assayed for serum IgG and, where indicated, mucosal IgA antibodies directed against OVA, BSA, and LT by ELISA. The number of animals in each immunization group is included in the legend to each figure.

6.3. ANTIBODY ASSAY

Animals were bled prior to euthanasia and sera were stored at −20° C. until assayed. The small intestine from duodenum to ileal-cecal junction was excised and homogenized in a solution containing 50 mM EDTA and 0.1 mg per ml of Soybean Trypsin Inhibitor (Sigma Chemical Co.). Samples were homogenized with a Tekmar Tissuemizer, clarified by centrifugation, lyophilized, resuspended in 1 ml of TEAN buffer, dialyzed against TEAN buffer, adjusted to a constant volume, and stored at −20 C. until assayed.

6.4. ELISA

Reagents and antisera for the ELISA were obtained from Sigma Chemical Co. Samples for ELISA were serially diluted in phosphate buffered saline (pH 7.2)-0.05% Tween 20 (PBS-TWEEN). For anti-LT determinations, microtiter plates were precoated with 1.5 $\mu$g per well of mixed gangliosides (Type III), then with 1 $\mu$g per well of purified LT-B. Anti-OVA and anti-BSA were determined on microtiter plates precoated with 10 $\mu$g per well of OVA or 10 $\mu$g per well of BSA, respectively. Serum anti-LT, anti-OVA, and anti-BSA IgG were determined with rabbit antiserum against mouse IgG conjugated to alkaline phosphatase. Mucosal anti-LT, anti-OVA, and anti-BSA IgA were assayed with goat antiserum against mouse IgA [alpha-chain specific] followed by rabbit antiserum against goat IgG conjugated to alkaline phosphatase. Reactions were stopped with 3N NaOH. Values for IgG and IgA were determined from a standard curve with purified mouse myeloma proteins (MOPC 315, $\gamma$A(IgA$\lambda$2); MOPC 21, $\gamma$G1: Litton Bionetics, Inc., Charleston, S.C). Cross reactivity was determined by crossing reagents as described (Clements et al., 1986). Mucosal IgA values are further corrected for contamination of mucosa with serum (Corrected Mucosal IgA=Mucosal IgA−[Serum IgA×{Mucosal IgG/Serum IgG}]).

6.5. USE OF LT AS AN ADJUVANT WITH HERPES SIMPLEX VIRUS

The procedures for immunization were essentially as described above. Four groups of mice, each containing seven to nine animals, were immunized as follows: On day 0, Group A received 0.5 ml of PBS containing 5 mg of OVA, 20 $\mu$g of u-v inactivated Herpes simples virus type 1 [HSV(uv)], and 25 $\mu$g of LT; Group B received 0.5 ml of PBS containing 20 $\mu$g of HSV(uv) and 25 $\mu$g of LT; Group C received 0.5 ml of PBS containing 20 $\mu$g of viable HSV; and Group D received 0.5 ml of PBS containing 20 $\mu$g of HSV(uv). This regimen was repeated on days 7 and 14. On day 21, animals were boosted i.p. with 0.5 ml of PBS containing 1 $\mu$g of HSV(uv) in 20% Maalox. Serum IgG and mucosal IgA responses were determined one week later for HSV by ELISA using microtiter plates precoated with 10 $\mu$g per well of HSV(uv).

6.6. NEUTRALIZATION OF HSV-1 BY ANTISERUM AGAINST ORALLY ADMINISTERED, U-V INACTIVATED HSV-1

Sera from mice which had been immunized with u-v inactivated HSV-1 were added to aliquots of HSV-1. The mixtures were then used to infect monolayers of African Green Monkey Kidney (AGMK) cells. Cells were challenged with virus at a multiplicity of infection of 10 pfu per cell or mock infected in the presence of the mouse serum. After 18 hr, the ability of the mouse sera to neutralize HSV-1 infectivity was quantitated by counting the number of cells in each well which were rounded or spindle-shaped, the typical cytopathic effect (CPE) induced by HSV-1.

6.7. EFFECT OF LT ON TOLERANCE TO OVA

Four groups of BALB/c mice were immunized in this preliminary experiment. On day 0, each group was immunized orally as follows: Group A received 0.5 ml of PBS, Group B received 0.5 ml of PBS containing 5 mg of OVA, Group C received 0.5 ml of PBS containing 5 mg of OVA and 25 µg of LT, and Group D received 0.5 ml of PBS containing 5 mg of OVA and 17 µg of LT-B. Each regimen was administered again on days 7 and 14. On day 21, all animals were boosted i.p. with 1 µg of OVA in 20% Maalox (Table 1).

TABLE 1

Effect of LT on Oral Tolerance to OVA

| p.o | i.p. | IgG[a] | IgA[b] |
|---|---|---|---|
| PBS 3X | OVA | 95 ± 75 | — |
| OVA 3X | OVA | 35 ± 4 | — |
| OVA/LT 3X | OVA | 3,194 ± 2,150 | — |
| OVA/LT-B 3X | OVA | 40 ± 7 | — |

[a]µg/ml ±SEM as deterinined by ELISA. See text for details.
[b]Not determined.

As seen in FIG. 1, animals primed orally with OVA developed a significantly lower serum IgG anti-OVA response following subsequent parenteral immunization with OVA than those primed with PBS alone and subsequently immunized parenterally with OVA (FIG. 1B-35 µg/ml vs FIG. 1A-95 µg/ml). On the other hand, animals primed orally with OVA and LT developed a significantly higher serum IgG anti-OVA response than those in either of the other two groups (FIG. 1C-3,194 µg/ml). We observed that the simultaneous administration of LT with OVA not only prevented the induction of tolerance to OVA caused by oral feeding of OVA alone, but also acted as an adjuvant for the antigen, increasing the anti-OVA IgG response by approximately 90 fold over the response seen in animals fed OVA alone (tolerant) and approximately 30 fold over the response seen in animals fed only PBS prior to the i.p. immunization with OVA.

It was necessary to determine if the observed response was a function of the binding component of the molecule (LT-B) or of the enzymatically active subunit A. We were in a unique position to make this determination since LT-B derived from the holotoxin by dissociation chromatography is invariably contaminated with residual traces of LT, whereas our LT-B recombinant clone produces LT-B free of any contaminating subunit A (Clements and El-Morshidy, 1984, Infect. Immun. 46:564–569). Therefore, in place of LT we substituted an equimolar amount of LT-B (17 µg vs 25 µg). Also seen in FIG. 1, there were no significant difference between the group primed orally with OVA and LT-B (FIG. 1D-40 µg/ml) and that primed with OVA alone (FIG. 1B-35 µg/ml). Additional experiments failed to demonstrate any effect of LT-B on the induction of tolerance with levels of LT-B up to 100 µg, the highest amount tested (data not shown). These experiments suggested that the ability to abrogate the induction of tolerance is a function of the A subunit of LT, since LT-B alone was unable to influence tolerance induction. Presumably, the B subunit is required to facilitate penetration of the A subunit into the cell.

6.8. EFFECT OF VARYING THE TIMING AND ROUTE OF DELIVERY OF LT

Five groups of BALB/c mice were immunized as above. On day 0, each group was immunized orally as follows: Group A received 0.5 ml of PBS, Group B received 0.5 ml of PBS containing 5 mg of OVA, and Group C received 0.5 ml of PBS containing 5 mg of OVA and 25 µg of LT. This regimen was administered again on days 7 and 14. Group D received 0.5 ml of PBS containing 5 mg of OVA on day 0 and 0.5 ml of PBS containing 5 mg of OVA and 25 µg of LT on days 7 and 14.

Group E received 0.5 ml of PBS containing 5 mg of OVA on days 0 and 7 and 0.5 ml of PBS containing 5 mg of OVA and 25 µg of LT on day 14. On day 21, animals in Groups A through E were boosted i.p. with 1 µg of OVA in 20% Maalox (Table 2).

TABLE 2

Effect of Varying the Timing and Route of Delivery of LT

| p.o. | i.p. | IgG[a] | IgA[b] |
|---|---|---|---|
| PBS 3X | OVA | 16 ± 3.9 | ND[c] |
| OVA 3X | OVA | 11 ± 1.6 | 11 ± 11 |
| OVA/LT 3X | OVA | 6,889 ± 921 | 134 ± 35 |
| OVA 1X OVA/LT 2X | OVA | 2,186 ± 530 | ND |
| OVA 2X OVA/LTR 1X | OVA | 32 ± 18.9 | ND |
| OVA 3X[d] LT 3X | OVA | 11 ± 4.5 | ND |
| LT 3X[e] OVA 3X | OVA | 24 ± 4.8 | 10 ± 6 |
| OVA 3X | OVA/LT | 16 ± 3.9 | ND |
| OVA/LT 3X | OVA/LT | 6,099 ± 799 | 53 ± 39 |
| OVA/LT 1X | OVA | 4,499 ± 1,369 | 154 ± 54 |

[a]µg/ml ±SEM as determined by ELISA. See text for details.
[b]ng/ml ±SEM as determined by ELISA. See text for details.
[c]N.D. None detected.
[d]This group received 0.5 ml of PBS containing 5 mg of OVA on days 0, 7, and 14, and received 0.5 ml of PBS containing 25 µg of LT on days 1, 8, and 15.
[e]This group received 0.5 ml of PBS containing 25 µg of LT on days 0, 7, and 14, and received 0.5 ml of PBS containing 5 mg of OVA on days 1, 8, and 15.

As seen in FIG. 2, animals fed LT with OVA after a single initial OVA prime (FIG. 2D-2,186 µg/ml) or two initial OVA primes (FIG. 2E-32 µg/ml) developed significantly lower serum IgG anti-OVA responses than those in the group receiving LT with OVA in the initial immunization (FIG. 2C-6,889 µg/ml). This outcome could have resulted from either a timing-to-event phenomenon reflecting the shorter timing of LT administration prior to i.p. administration of the antigen or, conversely, could have represented a decreased effectiveness resulting from prior immunologic experience with the antigen (see below). The effect of LT administration on the development of mucosal IgA was also determined (FIG. 3). There was a significant increase in mucosal IgA anti-OVA (FIG. 3C-134 µg/ml) when LT was administered with the OVA during each of the three oral priming events. However, if the animals were immunized with OVA first, subsequent administration of LT with OVA failed to produce a detectable mucosal IgA anti-OVA response (FIG. 3D and FIG. 3E).

The effect of timing of the LT administration on production of serum IgG and mucosal IgA was also examined. Two groups of BALB/c mice were immunized for this study. Group F received 0.5 ml of PBS containing 5 mg of OVA on days 0, 7, and 14, and received 0.5 ml of PBS containing 25 µg of LT on days 1, 8, and 15. Group G received 0.5 ml of PBS containing 25 µg of LT on days 0, 7, and 14, and received 0.5 ml of PBS containing 5 mg of OVA on days 1, 8, and 15. As above, animals in both groups were boosted i.p. with 1 µg of OVA in 20% Maalox on day 21. Animals receiving LT before each administration of OVA had a slight but significantly higher level of serum IgG (FIG. 2G-24 µg/ml) anti-OVA than those orally primed with PBS alone (FIG. 2A-16 µg/ml), those orally primed with PBS containing OVA (FIG. 2B-11 µg/ml), or those orally primed with OVA the day before each administration of LT (FIG. 2F-11 µg/ml). The mucosal anti-OVA IgA response in animals receiving LT prior to OVA (FIG. 3G) was not significantly different from control values for animals primed with PBS (FIG. 3A) or with OVA alone (FIG. 3B).

Three additional groups of mice were immunized.

Group H received 0.5 ml of PBS containing 5 mg of OVA on days 0, 7, and 14. Group I received 0.5 ml of PBS containing 5 mg of OVA and 25 µg of LT an days 0, 7, and 14. On day 21, both groups of animals were boosted i.p. with 1 Ag of OVA and 25 pg of LT in 20% Maalox. Serum IgG (FIG. 2H-16 µg/ml) and mucosal IgA (FIG. 3H - no detectable response) anti-OVA responses in animals boosted parenterally with OVA and LT were not significantly different from control values.

Moreover, parenteral boosting with OVA and LT neither enhanced nor diminished the serum IgG (FIG. 2I-6,099 µg/ml) or mucosal IgA (FIG. 3I-53 nµg/ml) anti- OVA response when compared to animals receiving oral priming with OVA and LT and parenterally boosted with OVA alone (FIG. 2C-6,889 5µg/ml and FIG. 3C-134 nµg/ml).

The last group of animals in this series of experiments (Group J) received 0.5 ml of PBS containing 5 mg of OVA and 25 µg of LT on day 0, and 0.5 ml of PBS containing mg of OVA on days 7 and 14. On day 21, all animals in this group were boosted i.p. with 1 µg of OVA in 20% Maalox.

Interestingly, serum IgG (FIG. 2J-4,499 µg/ml) and mucosal IgA (FIG. 3J-154 nµg/ml) anti-OVA responses in animals receiving LT with OVA on only a single occasion, that being upon first exposure to the antigen, were not significantly different from those observed in animals receiving three oral priming doses with OVA and LT, thereby indicating that the alteration of the regulatory environment in the gut associated lymphoid tissue which shifts it toward responsiveness occurs early upon first exposure to the antigen and demonstrates memory in favor of responsiveness.

6.9. EFFECT OF PRIOR EXPOSURE TO OVA ON THE ABILITY OF LT TO INFLUENCE TOLERANCE TO OVA

For this experiment, six groups of BALB/c mice were immunized as above. On day 0, each group was immunized orally as follows: Groups A and D received 0.5 ml of PBS, Groups B, E, and F received 0.5 ml of PBS containing 5 mg of OVA, and Group C received 0.5 ml of PBS containing 5 mg of OVA and 25 µg of LT. This regimen was administered again on days 7 and 14. Groups A, B, and C received 0.5 ml of PBS p.o. on days 21, 28, and 35; while Groups D and E received 0.5 ml of PBS containing 5 mg of OVA and 25 µg of LT on those days. Group F continued to receive 0.5 ml of PBS containing 5 mg of OVA on days 21, 28, and 35. On day 42, all animals were boosted i.p. with 1 µg of OVA in 20% Maalox. On day 49, all animals were sacrificed and assayed for serum IgG and mucosal IgA antibodies directed against OVA and LT by ELISA (Table 3).

TABLE 3

Effect of Prior Exposure to OVA on the Ability of LT to Influence Tolerance to OVA

| p.o. | i.p. | IgG[a] | IgA[b] |
|---|---|---|---|
| PBS 6X | OVA | 87 ± 9 | .019 ± .016 |
| OVA 3X OBS 3X | OVA | 28 ± 6 | .055 ± .029 |
| OVA/LT 3X PBS 3X | OVA | 10,693 ± 5,005 | 29.7 ± 16.8 |
| PBS 3X OVA/LT 3X | OVA | 14,522 ± 2,848 | 8.6 ± 7.1 |
| OVA 3X OVA/LT 3X | OVA | 16 ± 3 | ND[c] |
| OVA 6X | OVA | 12 ± 1 | ND |
| LT 2X (i.p.) OVA/LT 3X | OVA | 958 ± 558 | ND |
| LT 2X OVAL/LT 3X | OVA | 1,505 ± +358 | .001 ± .00025 |

[a]µg/ml ±SEM as determined by ELISA. See text for details.
[b]µg/ml ±SEM as determined by ELISA. See text for details.
[c]N.D. None detected.

As seen in FIG. 4, tolerance was still induced and could still be prevented by coinoculation with LT, even when there was a three week delay between the final oral inoculation and the i.p. challenge (FIG. 4A-87 µg/ml; FIG. 4B-28 µg/ml; FIG. 4C-10,693 µg/ml). Group D (FIG. 4D-14,522 µg/ml) serves as a positive control for this section.

Group F shows the result of 6 weeks of oral feeding with OVA alone. Note the decreased response following 6 weeks of oral OVA (FIG. 4F-12 µg/ml) when compared to three weeks of oral feeding (FIG. 4B-28 µg/ml). This finding is consistent with previous observations that the larger doses produce a greater the degree of tolerance (Siskind, 1984). The differences between animals receiving LT with OVA after a 3 week oral prime with OVA (FIG. 4E-16 µg/ml) and those receiving OVA alone for either 3 weeks (FIG. 4B-28 µg/ml) or 6 weeks (FIG. 4F-12 µg/ml) were not statistically significant, thereby indicating that the observed effect is one of prevention of tolerance induction and not breaking of tolerance once established. Additionally, either prior parenteral administration of LT (FIG. 4G-958 µg/ml) or prior oral administration of LT (FIG. 4H-1,505 µg/ml) significantly reduced the ability of LT to prevent tolerance induction, raising the possibility that LT may not be effective in repeated exposures if anti-LT antibodies are present. Anti-LT IgG levels were 77,000 µg/ml and 2,000 µg/ml for Groups G and H, respectively. It is not known, however, if prior immunization with LT reduces the subsequent anti-OVA response below what would be protective levels in a system employing biologically relevant antigens. Animals immunized with LT prior to administration of OVA/LT had a significantly higher level of serum IgG anti-OVA than those orally primed with PBS alone (FIG. 4A-87 µg/ml), or those orally primed with PBS containing OVA (FIG. 4B-28 µg/ml).

The mucosal anti-OVA IgA responses in these groups was examined. As seen previously, mucosal anti-OVA IgA was present in detectable quantities only when OVA was administered with LT (FIG. 5C and FIG. 5D), and the response was greater with the extended time between oral feeding with OVA/LT and i.p. boost with OVA. It is important to note that IgA values in this six week protocol were enhanced compared to the previous three week protocol (µg/ml vs ng/ml), possibly a reflection of the prolonged period of feedings.

The fact that the anti-OVA response was greatly increased with the simultaneous administration of LT raised the possibility that LT could be used as an adjuvant for oral immunization to produce both a serum IgG and mucosal IgA response directed against the determinants of virulence of infectious agents.

6.10. USE OF LT AS AN ADJUVANT WITH TWO UNRELATED ANTIGENS

In order to test further the potential of LT as an orally administered adjuvant, three groups of mice were immunized as follows: On day 0, Group A received 0.5 ml of PBS, Group B received 0.5 ml of PBS containing 5 mg of OVA and 5 mg of BSA, and Group C received 0.5 ml of PBS containing 5 mg of OVA, 5 mg of BSA, and 25 µg of LT. This regimen was administered again on days 7 and 14. On day 21, each group of animals was boosted i.p. with 1 µg of OVA and 1 pg of BSA in 20% Maalox. Serum IgG and mucosal IgA responses were determined for both OVA and BSA. As seen in FIG. 6, simultaneous administration of LT with OVA and BSA increased the serum IgG response to OVA approximately 35 fold [FIG. 6 (upper left panel)B-302 µg/ml vs FIG. 6 (upper left panel)C-10,710 µg/ml] and increased the serum anti-BSA IgG response approximately 11 fold [FIG. 6 (upper right panel) B-1,035 µg/ml vs FIG. 6 (upper right panel)C-11,348 µg/ml]. A mucosal anti-OVA IgA response was only detected in animals receiving LT with the oral immunization [FIG. 6 (lower left panel)C-814 ng/ml]. There was no significant change in mucosal anti-BSA IgA following this regimen [FIG. 6 (lower right panel)], although it remains undetermined whether or not BSA administered with LT in the absence of OVA would provoke an increased response. Interestingly, there was no detectable anti-OVA or anti-BSA serum IgG response when OVA and BSA were administered i.p. following p.o. priming with PBS alone. This was different than the response observed with p.o. administration of OVA alone following PBS priming and may reflect the consequence of administering the combined antigens. Specifically, our experience indicates that prior exposure to an antigen in the absence of LT reduces or eliminates the subsequent ability of LT to influence the antibody response to that antigen when administered orally. Most commercial laboratory rodent foods are contaminated with BSA and this may have influenced the observed results (Table 4).

TABLE 4

Use of LT as an Adjuvant with Two Unrelated Antigens

| | | IgG[a] | | IgA[b] | |
|---|---|---|---|---|---|
| p.o. | i.p. | anti-OVA | anti-BSA | anti-OVA | anti-BSA |
| PBS 3X | OVA/BSA | NDC | ND | ND | 334 ± 81 |
| OVA/BSA 3X | OVA/BSA | 302 ± 182 | 1,035 ± 594 | ND | 422 ± 180 |
| OVA/BSA/LT 3X | OVA/BSA | 10,710 ± 4,809 | 11,348 ± 4,273 | 814 ± 282 | 385 ± 83 |

6.11. EFFECT OF ROUTE OF IMMUNIZATION ON ANTI-OVA RESPONSE

For this experiment, four groups of BALB/c mice were immunized. On day 0, each group was immunized orally as follows: All groups received 0.5 ml of PBS containing 5 mg of OVA and 25 µg of LT. This regimen was administered again on days 7 and 14. On day 21, animals in Group A received a subcutaneous (s.c.) boost with 1 µg of OVA in 20% Maalox; Group B was boosted intramuscularly (i.m.) with 1 µg of OVA in 20% Maalox; Group C was boosted i.p. with 1 µg of OVA in 20% Maalox; and Group D was not boosted (Table 5).

TABLE 5

Effect of Route of Immunization on Anti-OVA Resodnses

| p.o. | i.p. | IgG[a] | IgA[b] |
|---|---|---|---|
| OVA/LT 3X | OVA (s.c.) | 2,829 ± 900 | 614 ± 386 |
| OVA/LT 3X | OVA (i.m.) | 877 ± 245 | 514 ± 210 |
| OVA/LT 3X | OVA (i.p.) | 4,668 ± 1,831 | 302 ± 100 |
| OVA/LT 3X | NONE | 105 ± 58 | 1,846 ± 974 |

[a]µg/ml ±SEM as determined by ELISA. See text for details.
[b]ng/ml ±SEM as determined by ELISA. See text for details.

Figure 7A:
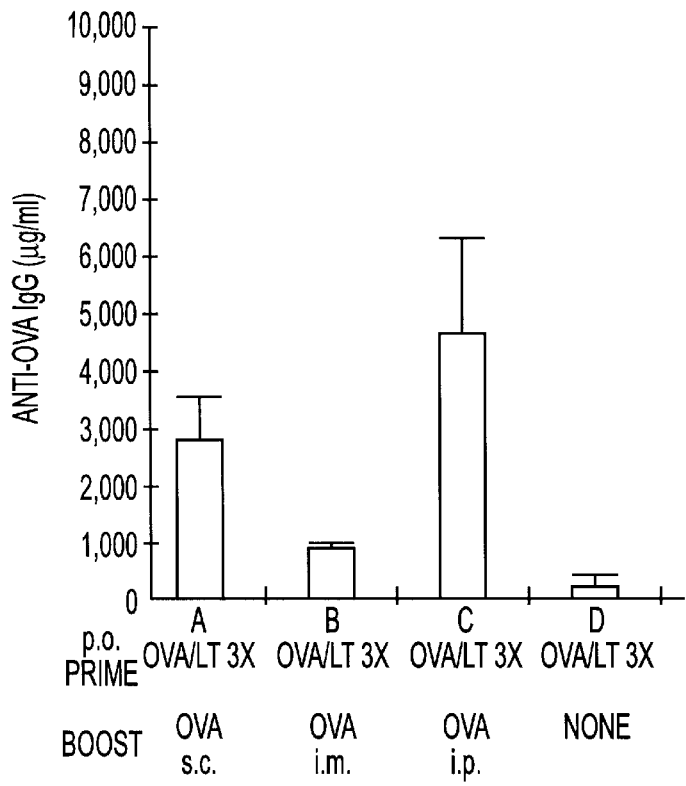
Figure 7B:
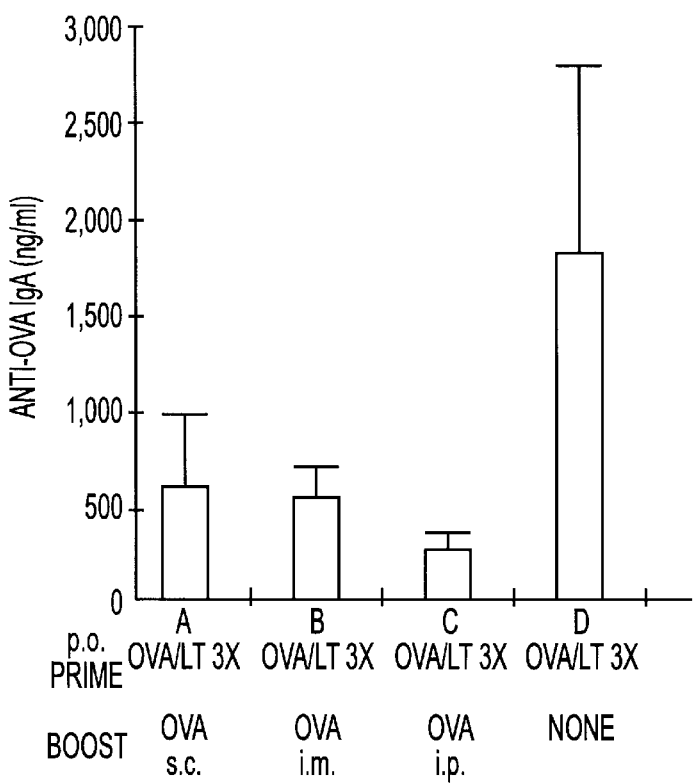

As seen in the upper panel of FIG. 7, groups of mice boosted i.p. with OVA developed significantly higher levels of serum IgG anti-OVA (FIG. 7C-4,668 µg/ml) than those boosted either s.c. (FIG. 7A-2,829 µg/ml) or i.m. (FIG. 7B-877 µg/ml) with OVA. The differences in serum anti-OVA IgG between groups boosted s.c. with OVA and control values for animals primed with PBS or with OVA alone and boosted i.p. with OVA were not statistically significant, while the differences in serum anti-OVA IgG between groups boosted i.m. with OVA and control values or animals primed with PBS or with OVA alone and boosted i.p. with OVA were statistically significant (not shown). The mucosal anti-OVA IgA responses in animals boosted by any of the three routes were not statistically significantly different from one another [FIG. 7 (lower panel)]. Importantly, animals that were not boosted (FIG. 7D) failed to develop a significant serum IgG anti-OVA response ([FIG. 7D (upper panel)-105 µg/ml] but did develop a significant mucosal IgA anti-OVA response ([FIG. 7D (lower panel)-1,846 ng/ml].

6.12. USE OF LT AS AN ADJUVANT WITH HERPES SIMPLEX VIRUS

In order to test the potential of LT as an orally administered adjuvant with a biologically relevant antigen, four groups of mice, each containing seven to nine animals, were immunized as follows: On day 0, Group A received 0.5 ml of PBS containing 5 mg of OVA, 20 µg of u-v inactivated 5Herpes simples virus type 1 [HSV(uv)], and 25 µg of LT; Group B received 0.5 ml of PBS containing 20 Ag of HSV(uv) and 25 Mg of LT; Group C received 0.5 ml of PBS containing 20 µg of viable HSV; and Group D received 0.5 ml of PBS containing 20 pg of HSV(uv). This regimen was repeated on days 7 and 14. On day 21, animals were boosted i.p. with 0.5 ml of PBS containing 1 µg of HSV(uv) in 20% Maalox.

Serum IgG and mucosal IgA responses were determined one week later for HSV by ELISA using microtiter plates precoated with 10 μg per well of HSV(uv). As seen in FIG. 8, simultaneous administration of LT with HSV(uv) enhanced the serum IgG response against HSV [FIG. 8 (left panel)A-61.47 ng/ml; B-81.74 ng/ml] when compared to animals immunized with HSV(uv) alone [FIG. 8 (left panel) D-5 4.46 ng/ml] or infected with viable HSV [FIG. 8 (left panel) C-27.00 ng/ml]. A mucosal anti-HSV IgA response was detected in animals receiving LT with the oral immunization in the presence of 5 mg of OVA [FIG. 8 (right panel)A-1.96 ng/ml] and in animals infected with viable HSV [FIG. 8 (right panel)C-0.07 ng/ml]. Interestingly, there was no detectable anti-HSV IgA response in animals immunized with HSV(uv) without the OVA included.

Since not all antibodies which react with virion proteins are capable of virus neutralization, it was necessary to determine if the antibodies produced in response to immunization were capable of neutralizing virus infectivity. For the virus neutralization assay, African Green Monkey Kidney Cells (AGMK) cells were seeded in 96-well tissue culture dishes at $5 \times 10^4$ cells per well. Sera of mice from the various groups were added to the cultures in two-fold serial dilutions. Cells were then challenged with HSV-1 at a multiplicity of infection of 10 pfu per cell or mock infected in the presence of the mouse serum. After 18 hr, the ability of the mouse sera to neutralize HSV-1 infectivity was quantitated by counting the number of cells in each well which were rounded or spindle-shaped, the typical cytopathic effect (CPE) induced by HSV-1. As seen in FIG. 9, the serum antibodies raised in mice immunized with LT and HSV(uv), with or without OVA, were able to protect AGMK cells against the cytopathic effects of HSV-1.

6.13. USE OF LT AS AN ADJUVANT FOR INDUCTION OF CAMPYLOBACTER INTESTINAL PROTECTIVE IMMUNITY

Campylobacter species constitute a family of organisms that have recently been shown to be the most frequent cause of bacterial gastroenteritis in humans. Campylobacter is second only to enterotoxigenic *Escherichia coli* (ETEC) as a cause of "travelers" diarrhea in civilian and military personnel. Like ETEC, it is acquired from drinking contaminated water or unpasteurized milk, and is endemic in many developing nations. In 1990, during operational exercises in the Far East involving U.S. forces, 6% of the participants developed reported diarrhea; 41%/c of the pathogens isolated were Campylobacter species. Major outbreaks have also occurred in the U.S. *Campylobacter coli, Campylobacter jejuni*, and *Helicobacter pylori* are the primary species implicated in human disease.

Because of its military significance, studies have been conducted at the Navy Medical Research Institute, Bethesda, MD., in collaboration with the inventor, to determine the utility of LT as an adjuvant for induction of protective immunity against two pathogenic strains of Campylobacter in three species of experimental animals.

Mouse Studies: FIGS. 11–14 illustrate the intestinal IgA response to different oral dose regimens of killed Campylobacter with or without LT adjuvant. Dose of antigen, species of antigen, mode of killing the bacteria for antigen preparation, and times of administration of antigen vary, but in all cases killed bacteria are suspended in phosphate buffered saline (PBS) and are delivered by oral gavage combined with 25 μg of LT on three different occasions. In all but the last model, the last oral administration is followed one week later by an i.p. boost with killed bacteria in PBS alone.

In FIG. 11, animals were given 300μg Lior serotype 8 *C. coli*. strain VC 167, killed by sonication (son), orally 3 times at weekly intervals without LT (filled circles), together with 25 μg LT (open circles) or, alternatively, were given 300μg live *C. coli* (filled squares) without adjuvant. The relative concentration of IgA antibody directed at *Campylobacter coli* extract is reflected by the optical absorbance at 405 nm (the Y-axis) plotted against decreasing concentrations of intestinal lavage fluid on the X-axis (ml $\log_{10}$). The data show that the IgA response to killed *C. coli* administered with LT is identical to the response stimulated by live organisms. In contrast, the response to killed *C. coli* without LT is substantially less.

FIG. 12 illustrates the intestinal IgA responses to various oral doses (50, 100 or 300 μg) of *C. coli*, strain VC 167, live or killed by sonication and combined with 25 μg LT, following 0 (unimmunized control), 1, 2 or 3 oral immunizations. These data show that at least 2 oral immunizations of killed bacteria and LT are required to achieve comparable levels of IgA that to induced by live bacteria. Further, they reveal that when sufficient (300 μg) killed bacterial antigen is administered in the presence of LT on 3 successive weeks, the intestinal IgA response exceeds that achieved by oral immunization with comparable amounts of live bacteria.

FIG. 13 illustrates the protective immunity induced by the optimal regimen demonstrated in FIG. 12, i.e., three weekly oral administrations of 300 μg of *C. coli* strain VC 167, killed by sonication and combined with 25 μg LT, compared to that induced by 300 μg of live *C. coli*. The Y-axis shows the percent of animals shedding live bacteria in their fecal pellets at various times (X-axis) following oral challenge with $2 \times 10_{10}$ colony forming units of live*C. coli* strain VC 167 or with the unrelated Lior serotype strain HC. The data indicate that 60% of mice orally immunized with killed bacteria plus LT (open circles) develop specific (for strain VC 167), protective immunity (ability to block colonization with live bacteria) compared to 100% of mice orally immunized with live bacteria (open squares). No protective immunity is induced to the unrelated strain HC (open triangles).

In FIG. 14, a different antigen preparation and a different immunization time course is employed similar to that employed in the rabbits studies described below. The data illustrate that improved protective immunity is induced by 3 oral administrations at 48 hr intervals of killed $10_5$ *C. jejuni* (a 1:1 mixture of 61YC heat-killed and Formalin-killed organisms), with (closed circles) or without (open circles) 25 μg LT, compared to unimmunized controls (crosses). These data demonstrate complete protection (100% resistance to colonization) against oral challenge with $2 \times 10_{10}$ colony forming units of live *C. jejuni*, a dose that colonized all unimmunized controls and 40% of mice immunized with killed bacteria in the absence LT.

Rabbit Studies: Young rabbits were immunized with *C. coli*, strain VC167, in a manner similar to that employed in the last mouse study described except that the bacteria ($10_{10}$) were killed by sonication and were delivered in 5% sodium bicarbonate. A so-called RITARD challenge model was used in which intestinal loops are made surgically with ligatures (to retard expelling of added contents by peristalsis) that can be loosened at will after the incision is closed. Previously immunized rabbits are challenged by injection of these loops with either live strain VC167, or with an unrelated Lior serotype, strain 81116. Establishment of colonization in these loops is determined by sampling the contents for live bacteria 5 days after challenge. Representative data from this type of study are given in Table 6 above. These data illustrate that only when the killed bacteria are delivered in combination with LT does significant resistance to homologous bacterial colonization take place (the 4th line of data). No protection is seen when the adjuvant is administered separately from the antigen (the 5th line of data). This resistance to colonization is specific for the Lior serotype of the antigen.

Monkey Studies: Rhesus monkeys were given $10_{10}$ *Campylobacter jejuni* cells killed by heat or Formalin in a 1:1 mixture combined with different concentrations of LT (0.5, 5.0 or 50 µg) and administered in 5%c sodium bicarbonate by oral gavage two times at weekly intervals. The animals were bled one week later and mononuclear leukocytes were isolated from the blood specimens. These cells were analyzed for the frequency of secretors of either IgA or IgG antibodies directed at either C. jejuni or the B subunit of LT (LTB). (LTB). The data from this study are provided in Table 7.

TABLE 7

Immunogenicity of Oral Campylobacter in Rhesus Monkeys

|  | Mean Antibody Secreting Cells/$10^6$ Circulating Mononuclears | | | |
|---|---|---|---|---|
|  | C. jejuni Ag | | E. Coli LTB Ag | |
| VACCINE GROUP | IgA | IgG | IgA | IgG |
| Pre-vaccination (n = 12) | 0 | 0 | 0 | 0 |
| Killed bacteria in vehicle (n = 2) | 3 | 31 | 1 | 5 |
| Killed bacteria + 0.5 µg LT (n = 3) | 5 | 41 | 1 | 11 |
| Killed bacteria + 5.0 µg LT (n = 3) | 14 | 56 | 5 | 19 |
| Killed bacteria + 50 µg LT (n = 3) | 14 | 38 | 13 | 15 |

These data suggest that the monkeys are relatively responsive to both bacterial antigen in the absence of adjuvant, and that low levels of secreting cells respond to LTB in the absence of specific treatment with LT (the 2nd line of data). Responses to both microbial antigens are enhanced when LT is co-administered. The optimal adjuvant dose would appear to be in the range of 5 µg.

6.14. USE OF LT AS AN ADJUVANT FOR INDUCTION OF PERSISTENT HUMORAL, CELLULAR AND PROTECTIVE IMMUNITY TO INFLUENZA IN THE LUNG

Influenza virus, while rarely immunologically lethal for healthy individuals, causes more clinical illness in First World populations than any other infectious agent. Lost work time as well as high mortality in infants and the elderly make influenza a major public health threat. The standard vaccine for influenza is comprised of Formalin-inactivated virus and alum salts as an adjuvant administered intramuscularly. This vaccine is ineffective at stimulating respiratory mucosal immunity and its ability to protect the lung (the target organ of influenza) is limited to a brief period of time when serum IgG levels are high enough to spill over into the lung. In an effort to improve this inadequate vaccine design, Dr. Jacquelin Katz of the St. Jude Childrens Research Hospital, Memphis, TN, a major center for influenza research, collaborated with the inventor to determine the utility of LT for the induction of protective immunity to influenza virus in the mouse.

In all studies specific pathogen-free Balb/c mice were vaccinated 3 times by the oral route at 7 day intervals with Formalin-inactivated strain X31 virus (standard vaccine) suspended in 0.2 M sodium bicarbonate and containing between 25–50 µg of influenza hemagglutinin protein, with or without 25 µg of LT. Seven days later, the animals received an intraperitoneal boost with 10 µg of killed virus alone. The results of these studies are provided in FIG. 15 and in Tables 8–11.

FIG. 15 summarizes both serum lung IgG and IgA antibody responses determined by ELISA (expressed as $\log_{10}$ titers) using vaccine alone (Vac), 3 oral inoculations of vaccine and LT (Vac/LT), vaccine alone with the IP boost (Vac/IP), vaccine plus LT plus IP boost (Vac/LT/IP), IP boost alone (IP), or no immunization (None). The amount of antigen administered IP proved to be a potent stimulus (possibly via a newly-discovered mode of macrophage migration from the peritoneum to the lung), but addition of LT to the regimen improved all antibody responses as late as 3 months after completion of the immunization.

Tables 8–10 reveal a more marked effect of LT on cellular immunity measured in spleen lymphocyte cultures prepared 2–3 months following completion of the immunization. In these studies, IP immunization alone was ineffective at stimulating either cytolytic T cell activity (Table 8), IL-2 secretion (Table 9) or T cell proliferative activity (Table 10).

TABLE 8

Secondary CTL Response in Mice Receiving Oral Inactivated Influenza Vaccine in the Presence of LT Adjuvant

| CTL Effectors from Mice | % Specific $^{51}$Cr Release on KD$_2$ Targets Infected with: | | | |
|---|---|---|---|---|
| Vaccinated with[a] | A/X31 | A/PR8 | Type B | No Virus |
| Vac | 8.9 | 0 | 3.3 | 0 |
| Vac/LT | 26.4 | 10.5 | 2.2 | 2.0 |
| Vac/IP | 7.8 | 1.2 | 0 | 0 |
| Vac/LT/IP | 26.1 | 21.4 | 5.3 | 6.1 |
| IP | 0 | 1.6 | 0 | 0 |
| LT | 6.4 | 0 | 0 | 0 |
| X31 MLN[b] | 72.3 | 14.1 | 13.4 | 0 |

[a]Effector:Target ratio = 25:1
[b]As a positive control, the response of mediastinal lymph node cells from mice infected intranasally with live X31 virus was also determined

TABLE 9

Virus-Specific IL-2 Response of T Cells from Vaccinated Mice[a]

| Vaccine Protocol | IL-2 activity (mean cpm + SEM) in supernatants from cultures stimulated with[b] | | | |
|---|---|---|---|---|
|  | A/X31 | Type B | No Virus | Con A |
| Vac | 916 + 179 | 167 + 21 | 311 + 93 | 11992 + 145 |
| Vac/LT | 8033 + 412 | 651 + 36 | 200 + 9 | 11362 + 388 |
| Vac/IP | 285 + 23 | 262 + 5 | 384 + 35 | 13477 + 310 |
| Vac/LT/IP | 10491 + 172 | 207 + 17 | 570 + 13 | 10785 + 895 |
| IP | 255 + 16 | 151 + 5 | 161 + 6 | 13202 + 247 |
| LT[c] | 135 + 10 | 127 + 5 | 193 + 11 | 11820 + 576 |

[a]Supernatants were harvested after 72 hr of culture of 4 x $10^5$ spleen cells per well and 0.1 HAU virus, no virus or 0.7 µg Con A. Supernatants (50 µl) were then assayed for their ability to provide IL-2 for IL-2 dependent CTLL T cells (1 x $10^4$) in a 28 hr proliferation assay
[b]SEM = standard error of the mean
[c]Mice received 3 weekly oral doses of 25 µg LT only

TABLE 10

Influenza (H3N2) HA-Specific Proliferative T Cell Response in Vaccinated Mice

| Vaccine Protocol[b] | Proliferative T Cell Response (SI)[a] | | | | | | |
|---|---|---|---|---|---|---|---|
|  | A/X31 '68 | A/Mem '72 | A/Vic '75 | A/Tex '77 | A/Bang '79 | A/Phil '82 | Type B |
| Vac | 1.3[c] | 3.0 | 2.1 | 1.5 | 1.3 | 1.3 | 1.2 |
| Vac/LT | 8.6 | 14.1 | 17.9 | 12.6 | 3.4 | 3.1 | 2.1 |
| Vac/IP | 4.1 | 13.6 | 12.0 | 3.3 | 3.6 | 2.5 | 2.9 |
| Vac/LT/IP | 10.7 | 28.4 | 33.7 | 25.6 | 4.2 | 3.3 | 2.1 |

TABLE 10-continued

Influenza (H3N2) HA-Specific Proliferative T Cell Response in Vaccinated Mice

| Vaccine Protocol[b] | Proliferative T Cell Response (SI)[a] | | | | | | |
|---|---|---|---|---|---|---|---|
| | A/X31 '68 | A/Mem '72 | A/Vic '75 | A/Tex '77 | A/Bang '79 | A/Phil '82 | Type B |
| IP | 1.2 | 1.9 | 3.4 | 1.1 | 1.1 | 1.6 | 1.4 |
| None | 1.2 | 2.1 | 2.4 | 1.7 | 1.0 | 1.9 | 1.4 |

[a]SI; stimulation index = $\frac{\text{test cpm}}{\text{control cpm}}$

[b]25 μg viral HA protein

[c]response to 0.01 HAU virus/well

All three responses are markedly enhanced compared to vaccine alone when the animals are given LT together with vaccine, regardless of whether an IP boost is used. Most striking is the LT-dependence of the cytolytic T cell response, a cell class known to be critical for the clearance of virus in influenza infections (Wyde, et al., 1977, Infect. Immun. 15:221–229).

In Table 11 preliminary data on protection against intranasal challenge with a lethal dose of influenza virus 3 months following completion of immunization are presented. These data indicate that the animals receiving LT at the time of immunization are completely protected, whether or not an IP boost is given.

TABLE 11

Protection of Mice from Reinfection 3 Months After Oral Vaccination

| Vaccine Protocol (25 μg) | Pre-Challenge Serum HI Antibody (GMT) | Response to Challenge | | |
|---|---|---|---|---|
| | | Total Number Shedding | Virus Titer in Lung ($\log_{10}$ $EID_{50}$/ml) | Percent Protection |
| 1. Vac | <10 | 2/5 | 2.7 | 60 |
| 2. Vac/LT | 26 | 0/5 | < | 100 |
| 3. Vac/IP | 23 | 1/5 | 4.5 | 80 |
| 4. Vac/LT/IP | 138 | 0/5 | < | 100 |
| 5. IP | 17 | 2/4 | 2.3 | 50 |
| 6. None | <10 | 4/4 | 5.7 | 0 |

These findings are consistent with the enhanced cellular immunity seen in animals immunized with LT adjuvant, in particular the cytolytic T cell class.

6.15. SUMMARY OF IN VIVO STUDIES WITH LT ORAL ADJUVANT

The data presented in this section demonstrate that LT functions as an adjuvant when presented via the oral route on at least two occasions separated in time by at least 48 hours together with various non-living microbial antigens. Further, the data indicate that protective immunity is induced by LT against pathogenic viruses and bacteria inactivated by various means. A summary of these animal data are presented in Table 12, which demonstrates the variety of antigen forms, target species and dosage regimens with which LT oral adjuvant (LT-OA) has been shown to be efficacious to date.

TABLE 12

Summary of Animal Study Protocols

| ANTIGEN | SPECIES | AG DOSE | LT-OA DOSE-μg | DOSE INTERVAL | NUMBER OF DOSES |
|---|---|---|---|---|---|
| Ovalbumin and/or Bovine Serum Albumin | mouse-Balb/e female | 5 mg | 25 | 7 days | 3× i.g. in DBS + 1× i.p. malox, s.c. or i.m. |
| Herpes simplex-1, UV-killed virus | mouse | 20 μg | 25 | 7 days | 3× i.g. in PBS + 1× i.p. malox, s.c. or i.m. |
| Campylobacter- killed by heat or sonication (mix) | mouse-Balb/c female | 300 μg or $10^5$, $10^7$ or $10^9$ cells | 25 | 7 days or 2 days | 3× i.g. in PBS + 1× i.p. PBS |
| Campylobacter- killed by heat or sonication (mix) | rabbit | $10^{10}$ colony forming units | 25 | 2 days | 3× i.g. in 5% bicarb (no boost) |
| Campylobacter- killed 60° C. + merthiol or formalin (mix) | Rhesus monkey | $10^{10}$ cells | 0.5, 5, 15, 25, 50, 100, 500, 1000 | 14 days | 2× i.g. in 5% bicarb (no boost) |
| Influenza X31 H3N2 formalin-killed virus | mouse, Balb/c | 10 or 50 μg HA | 25 | 7 days | 3× i.g. 0.2 M bicarb + 1× i.p. PBS |

In view of the broad range of immune responses potentiated by LT-OA, it will be apparent to those skilled in the art that LT-OA can serve to potentiate enhanced immunity to a broad range of bacterial, viral, fungal and other microbial pathogens.

What is claimed is:

1. A method of increasing an immune response of a host to a specific pathogen which comprises orally administering to the host at least one dose of an admixture of an effective amount of an antigen specific for the pathogen and an adjuvant effective, non-toxic amount of *E. coli* heat labile enterotoxin (LT) in an orally acceptable pharmaceutical composition.

2. The method of claim 1 wherein the admixture contains a buffer.

3. The method of claim 1 wherein a mucosal immune response is produced.

4. The method of claim 1 wherein the admixture is administered as a single dose.

5. The method of claim 2 wherein the admixture is administered as a single dose.

6. The method of claim 1 wherein the antigen is a killed pathogen selected from the group consisting of bacteria, viruses, protozoa, and fungi.

7. The method of claim 6 wherein the pathogen is a bacterium.

8. The method of claim 7 wherein the bacterium is a campylobacter species.

9. The method of claim 6 wherein the pathogen is a virus.

10. The method of claim 9 wherein the virus is a herpes virus.

11. The method of claim 9 wherein the virus is an influenza virus.

12. An orally administrable pharmaceutical composition useful in producing a protective immune response in a host to an antigen specific for a pathogen comprising an admixture of an effective amount of the antigen and an adjuvant effective, non-toxic amount of *E. coli* heat labile enterotoxin (LT) in an orally acceptable pharmaceutical composition.

13. The composition of claim 12 wherein the pathogen is a bacterium.

14. The composition of claim 13 wherein the bacterium is a campylobacter species.

15. The composition of claim 12 wherein the antigen is a killed pathogen selected from the group consisting of bacteria, viruses, protozoa, and fungi.

16. The composition of claim 15 wherein the pathogen is a virus.

17. The composition of claim 16 wherein the virus is a herpes virus.

18. The composition of claim 17 wherein the virus is an influenza virus.

* * * * *